United States Patent [19]

Shishido et al.

[11] Patent Number: 5,410,400
[45] Date of Patent: Apr. 25, 1995

[54] FOREIGN PARTICLE INSPECTION APPARATUS

[75] Inventors: Hiroaki Shishido; Minori Noguchi, both of Yokohama, Japan

[73] Assignee: Hitachi, Ltd., Tokyo, Japan

[21] Appl. No.: 902,819

[22] Filed: Jun. 23, 1992

[30] Foreign Application Priority Data

Jun. 26, 1991 [JP] Japan .................. 3-154572
Sep. 19, 1991 [JP] Japan .................. 3-239480

[51] Int. Cl.[6] ........................................ G01N 21/88
[52] U.S. Cl. ........................... 356/237; 356/239; 250/572; 382/8
[58] Field of Search ............... 356/237, 239, 336, 337, 356/338, 394, 445, 446, 429-431; 250/562, 563, 572, 574; 358/101, 106, 107; 382/1, 8, 31, 65

[56] References Cited

U.S. PATENT DOCUMENTS

| | | | |
|---|---|---|---|
| 4,342,515 | 8/1982 | Akiba et al. | |
| 4,669,875 | 6/1987 | Shiba et al. | 356/237 |
| 4,681,442 | 7/1987 | Wagrer | 356/237 |
| 4,816,686 | 3/1989 | Hara et al. | 356/237 |
| 4,922,308 | 5/1990 | Noguchi et al. | 356/237 |
| 4,952,058 | 8/1990 | Noguchi et al. | |
| 5,046,847 | 9/1991 | Nakata et al. | |
| 5,235,400 | 8/1993 | Terasawa et al. | 356/237 |

FOREIGN PATENT DOCUMENTS

| | | |
|---|---|---|
| 54-101390 | 8/1979 | Japan . |
| 56-132549 | 10/1981 | Japan . |
| 57-80546 | 5/1982 | Japan . |
| 59-65428 | 4/1984 | Japan . |
| 60-38827 | 2/1985 | Japan . |
| 60-154634 | 8/1985 | Japan . |
| 60-154635 | 8/1985 | Japan . |
| 61-104242 | 5/1986 | Japan . |
| 61-104244 | 5/1986 | Japan . |
| 61-104659 | 5/1986 | Japan . |
| 63-315936 | 12/1988 | Japan . |
| 1-117024 | 5/1989 | Japan . |
| 1-153943 | 6/1989 | Japan . |

OTHER PUBLICATIONS

Kubota, H. "Applied Optics" (Iwanami Zensho), pp. 114-115, 128-137 and 144-149. (Provided in Japanese) (Published May, 1971, in Japan).

Wolf. "Principles of Optics," pp. 647-664. (Provided in English) (Published 1970 4th edition in Great Britain).

*Primary Examiner*—Hoa Q. Pham
*Attorney, Agent, or Firm*—Fay, Sharpe, Beall, Fagan, Minnich & McKee

[57] ABSTRACT

A foreign particle inspection apparatus includes a detection optical system (4) for condensing scattered light generated by slant illumination (2) by an optical system (41) with a NA of more than 0.4 from the rear side of a sample using a transparent or semitransparent substrate having an opaque circuit pattern. The circuit pattern, such as a reticle, etc., has a phase shift film for improving the patterning resolution, for shielding diffracted light from the circuit pattern by a spatial filter (44) mounted on the Fourier transform plane, and for forming images on a detector (51). A circuit (113) is also provided for correcting detected values of the detector according to uneven illumination, and a circuit for obtaining the added value of detected values of 2 by 2 pixels. A circuit (114) is provided for obtaining the maximum value of four added values which are shifted pixel by pixel in the four directions around each detector pixel. A circuit (112) is provided for storing the detected result in a memory where the substrate sample is divided into blocks every several hundreds pixels. By this arrangement small foreign particles of the order of submicrons adhered on the substrate can be separated and detected easily and stably from the circuit pattern principally using a simple optical structure.

11 Claims, 31 Drawing Sheets

EMBODIMENT OF PRESENT INVENTION

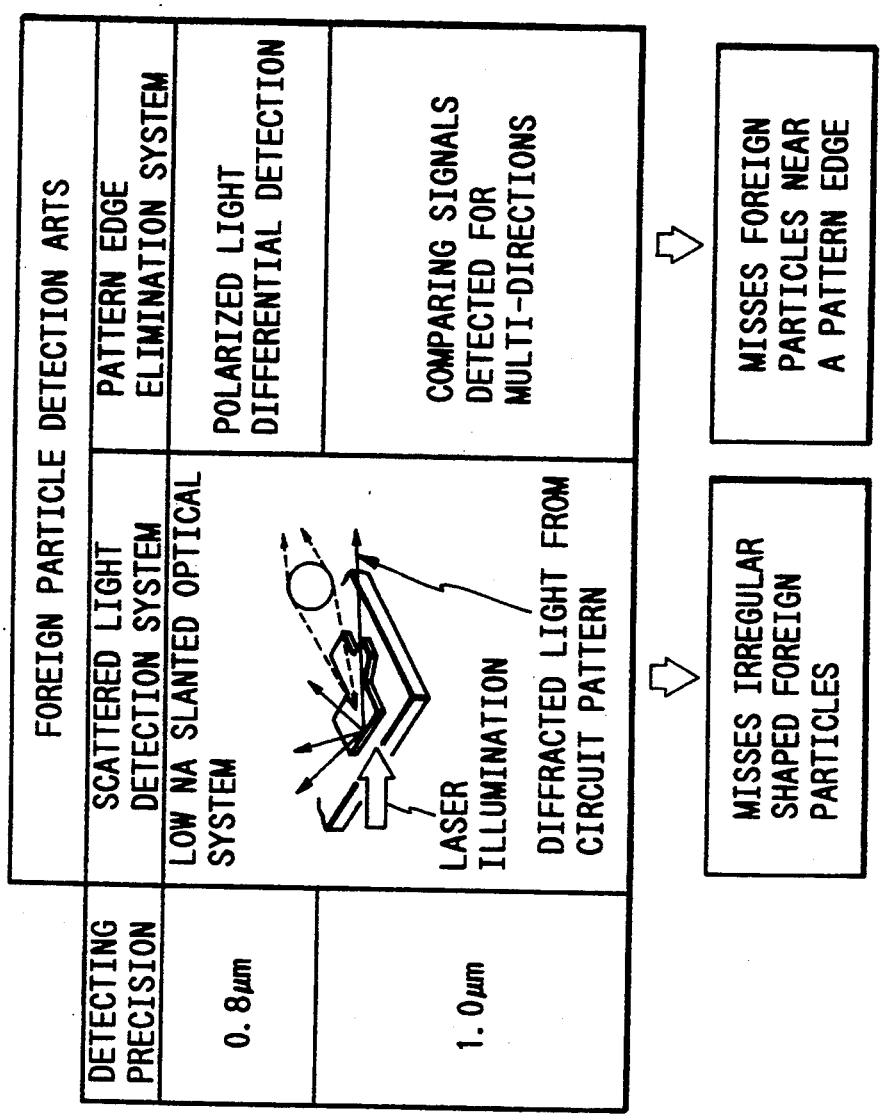

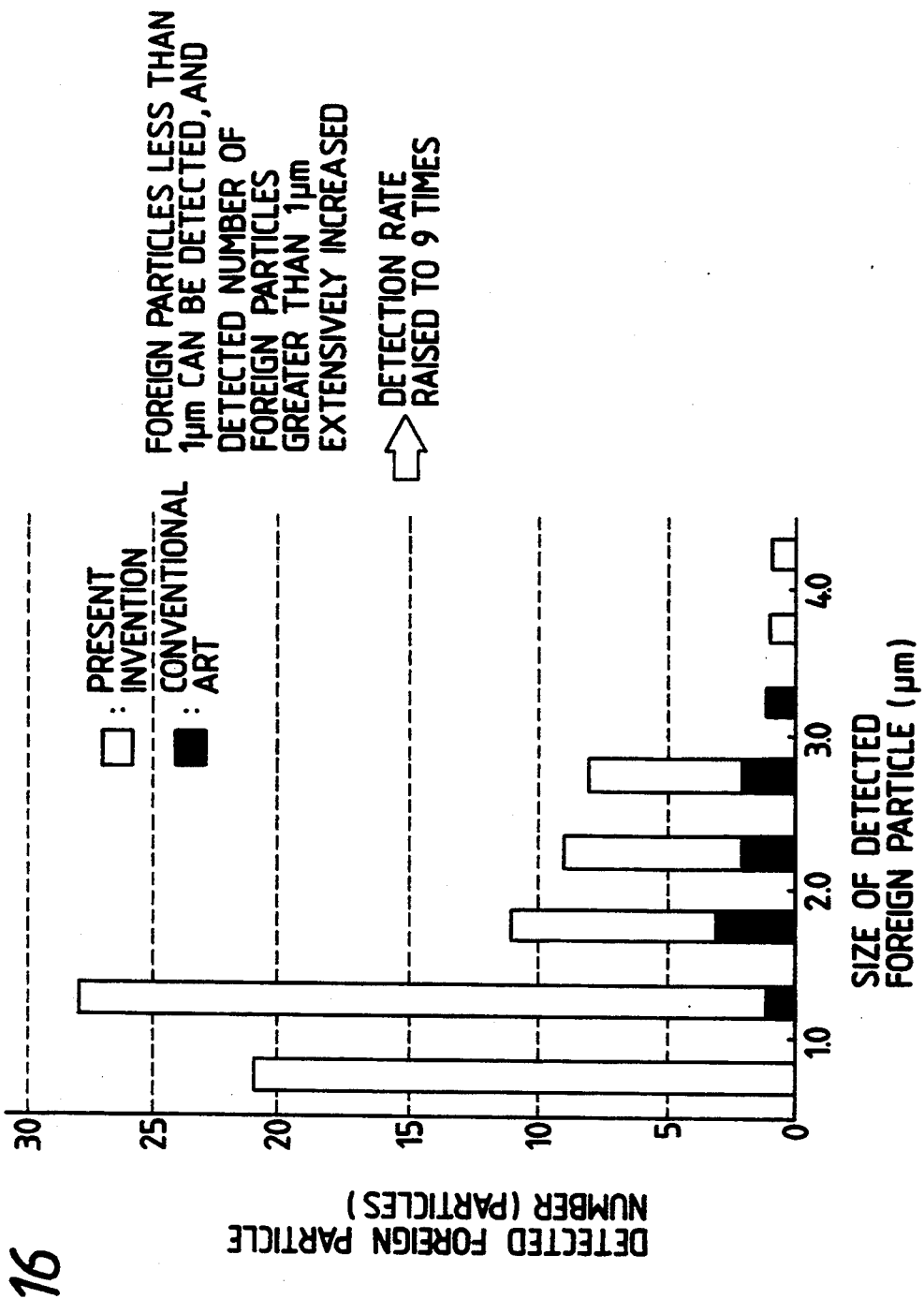

MEASURED RESULT
OF SHADING

COMPENSATED DATA
OF SHADING

DETECTED SIGNAL FROM A
COMPENSATED DETECTOR

FOREIGN PARTICLE INSPECTION APPARATUS

BACKGROUND OF THE INVENTION

1. Field of the Invention

The present invention relates to a foreign particle inspection apparatus for detecting foreign particles adhered on circuit patterns such as reticles or photomasks (hereinafter called reticles, etc.). More specifically, the invention relates to a foreign particle inspection apparatus (the inspection is performed before the circuit patterns are transferred to a wafer) for detecting small foreign particles of the order of submicrons on the above reticles, particularly on reticles having a phase shift film for improving the patterning resolution by a simple structure.

2. Description of the Prior Art

In the exposure process of reticles, etc. used for manufacturing LSIs or PCBs, each circuit pattern such as a reticle is inspected before it is baked and transferred onto a wafer. However, there is a problem imposed that even when small foreign particles, for example, of the order of microns are adhered on the above circuit pattern, the above circuit pattern is not correctly transferred onto a wafer due to the above foreign particles, and hence all of the LSI chips become defective. This problem is getting more remarkable due to recent high integration of LSIs and the existence of smaller foreign particles of the order of submicrons is not allowable.

To prevent the above defective transfer, it is essential to inspect foreign particles prior to the exposure process. Various foreign particle inspection techniques have been proposed for controlling reticles. For inspection of a circuit pattern such as a reticle, a method that a laser beam with superior directivity is irradiated slantwise onto it and scattered light generated from foreign particles is detected is advantageous from a view point of inspection speed and sensitivity and generally used.

In the above inspection method, however, diffracted light is also generated from the edge of the circuit pattern such as a reticle and a means for discriminating and detecting only foreign particles from the diffracted light is necessary and the techniques for that purpose are disclosed as shown below.

The first one of them is a foreign particle inspection apparatus comprising a linearly polarized laser, a means for irradiating the above laser beam slantwise at a specific incident angle, and a slant imaging optical system using a polarizing plate and lenses as disclosed, for example, in Japanese Patent Laid-Open No. 54-101390 (U.S. Pat. No. 4,342,515). The apparatus detects only foreign particles which are made bright by using the character that when linearly polarized light is irradiated onto a circuit pattern, the diffracted light from the circuit pattern and the scattered light from the foreign particles are different in the light polarizing direction from each other.

The second one of them is a foreign particle inspection apparatus comprising a means for irradiating and scanning a laser beam slantwise onto an inspection sample, a first lens which is installed above the inspection sample so as to allow the irradiation point of the above laser beam to almost coincide with its local point plane and condenses scattered light of the above laser beam, a shutter which is installed on the Fourier transform plane of the above first lens and shields regularly diffracted light from the circuit pattern of the inspection sample, a second lens for subjecting scattered light from foreign particles which is obtained via the shutter to an inverse Fourier transform, a slit which is installed at the imaging point of the above second lens and shields scattered light from other than the laser beam irradiation point on the inspection sample, and a light receptor for receiving the scattered light from the foreign particles which passes through the above slit, which is disclosed in, for example, Japanese Patent Laid-Open No. 59-65428, Japanese Patent Laid-Open No. 01-117024 (U.S. Pat. No. 5,046,847) and, Japanese Patent Laid-Open No. 01-153943.

In consideration of that the circuit pattern is generally structured in the same direction or by a combination of two or three directions in the view field, the above apparatus eliminates the diffracted light by the circuit pattern in this direction by a spatial filter installed on the Fourier transform plane so as to emphasize and detect only the scattered light from the foreign particles.

The third one of them is a foreign particle inspection apparatus of a structure that foreign particles are discriminated by ANDing detection outputs of a plurality of detectors which are installed slantwise in consideration of that diffracted light generated at the circuit pattern edge is directive but scattered light by foreign particles is not directive as disclosed, for example, in Japanese Patent Laid-Open No. 57-80546.

The fourth one of them is a foreign particle inspection apparatus for discriminating foreign particles by arranging a plurality of detectors using a phenomenon that diffracted light from the circuit pattern edge is focused only in a predetermined direction, while light generated by the foreign particles is scattered in all directions as disclosed, for example, in Japanese Patent Laid-Open No. 60-154634 and Japanese Patent Laid-Open No. 60-54635. When an array detector such as a one-dimensional solid imaging device, foreign particles are detected among pixels constituting the array and the output from the foreign particles is dispersed and detected into a plurality of pixels. As a result, the output from the detector becomes small in correspondence with dispersion and there is a possibility to miss foreign particles.

The fifth one of them is a foreign particle inspection apparatus using a method that array detectors are installed with an inclination to the scanning direction of the sample stage as disclosed in Japanese Patent Laid-Open No. 61-104242 or using a method that specially shaped array detectors are specially arranged as disclosed in Japanese Patent Laid-Open No. 61-104659 and, so as to avoid the above missing of foreign particles. Uneven or variable illumination affects the revivability and accuracy of detection.

The sixth one of them is a foreign particle inspection apparatus providing automatic calibration using a standard sample wherein the intensity of scattered light is measured beforehand as disclosed, for example, in Japanese Patent Laid-Open No. 60-38827 and, The seventh one of them is a foreign particle inspection apparatus using a means for preventing misidentifying a large amount of scattered light generated from a large foreign particle as scattered light from a number of small foreign particles as disclosed in Japanese Patent Laid-Open No. 1981-132549.

Techniques on the Schrielen method, a phase contrast microscopy, and diffraction images of a finite light source as a method and apparatus relating to small foreign particle inspection are disclosed, for example, in H. Kubota, Applied Optics (Iwanami Zensho), pp. 129 to 136.

As mentioned above, as foreign particles to be detected become small, an increase in missing of foreign particles affecting the manufacture of LSIs comes into question.

In the first one of the prior arts mentioned above (for example, Japanese Patent Laid-Open No. 54-101390 and, since the difference between the polarizing direction of scattered light from small foreign particles and the polarizing direction of diffracted light from the circuit pattern edge is small, a problem such that the foreign particles cannot be discriminated and detected is imposed.

Next, in the second one of the prior arts mentioned above (for example, Japanese Patent Laid-Open No. 59-65428, Japanese Patent Laid-Open No. 01-117024, and Japanese Patent Laid-Open No. 1989-153943), scattered light from foreign particles is separated from diffracted light from the circuit pattern by the shutter and only the scattered light from the foreign particles is detected by the slit. This prior art has a characteristic that the detection mechanism is simplified because foreign particles are detected by a simple binarizing method. However, diffracted light from the transposition parts of the above circuit pattern has a low tendency to be one-sided at a specific location like diffracted light from the straight lines and the diffracted light from the transposition parts of the circuit pattern cannot be shielded perfectly by the above spatial filter.

Furthermore, since diffracted light generated from a circuit pattern having a fine structure pattern of the order of microns required by recent high integration of LSIs is similar to scattered light from foreign particles in behavior, the above tendency is growing moreover and it is practically difficult to separate and detect foreign particles from the circuit pattern by the simple binarizing method, causing a problem.

In each apparatus of the third one of the prior arts mentioned above (for example, Japanese Patent Laid-Open No. 57-80546) and the fourth one of the prior arts mentioned above (for example, Japanese Patent Laid-Open No. 60-154634 and Japanese Patent Laid-Open No. 60-154635 and, there are problems imposed that it is difficult to use an optical system having a sufficient condensing capability from a view point of the equipment structure and it is practically difficult to detect weak scattered light generated from small foreign particles.

In each apparatus of the fifth one of the prior arts mentioned above (for example, Japanese Patent Laid-Open No. 61-104244 and Japanese Patent Laid-Open No. 61-104242), there are problems imposed that it is necessary to manufacture special detectors arid use a special optical system from a view point of the equipment structure and the application cost goes up.

Furthermore, in the apparatus of the sixth one of the prior arts mentioned above (for example, Japanese Patent Laid-Open No. 60-038827 and,), there are difficulties in the structural accuracy for array detectors suited to high speed detection and for detection of small foreign particles.

Furthermore, in the apparatus of the seventh one of the prior arts mentioned above (for example, Japanese Patent Laid-Open No. 56-132549), there is a problem imposed that since only one point of a large foreign particle is assumed as a foreign particle, the shape of a particularly long and narrow foreign particle cannot be recognized correctly.

To improve the patterning resolution of circuit patterns on a reticle formed by a metallic thin film such as chromium, a reticle whereon transparent or opaque thin films (the film thickness is about odd number times of a half of the wave length of the exposure light source) which are called phase shift films or phase shifters are mounted between the circuit patterns thereon has been developed recently. Although this film is transparent or opaque, it has a structure which is several times as large as the circuit pattern (about 0.1 $\mu$m in thickness). Therefore, diffracted light from the film edge is several to several tens times as large as diffracted light from the conventional circuit pattern edge and the foreign particle detection sensitivity is extremely lowered. Various trials have been made so as to solve those problems (for example, Japanese Patent Laid-Open No. 63-315936 application No. 62-151121 (U.S. Pat. No. 4,952,058), though no satisfactory solutions to those problems are found yet.

Therefore, it is practically difficult to separate and detect foreign particles from the circuit pattern by a simple linear spatial filter, causing a problem.

SUMMARY OF THE INVENTION

The object of the present invention is to provide a foreign particle inspection apparatus, which is free from the problems inherent in the aforementioned prior art and which separates and detects small foreign particles of the order of submicrons adhered on a transparent or opaque substrate having a circuit pattern, particularly a circuit pattern such as a reticle, etc. having a phase shift film for improving the patterning resolution easily and stably from the circuit pattern using a simple optical structure principally.

To accomplish the above object, a foreign particle inspection apparatus according to the present invention is a foreign particle inspection apparatus for detecting foreign particles adhered on a transparent or opaque substrate sample having a circuit pattern, which comprises, an inspection stage having a stage for moving the above substrate sample loaded thereon freely in the X, Y, and Z directions and a drive control system thereof;

an illumination system for illuminating the front side of the above substrate sample whereon the circuit pattern is formed or the rear side thereof slantwise;

a condensing optical system for condensing scattered light and diffracted light generated on the above substrate sample by illumination of the above illumination system from the rear side of the substrate sample whereon the above circuit pattern is formed or the front side thereof;

a spatial filter which is installed on the Fourier transform plane of the above condensing optical system and shields diffracted light from the line part of the above circuit pattern;

a detection optical system for imaging the above circuit pattern on the basis of the above condensed and shielded light;

a detector installed on the imaging plane by the above detection optical system; and a signal processor for processing data from the above foreign particles on the basis of the output of the above detector.

Furthermore, another foreign particle inspection apparatus according to the present invention is a foreign particle inspection apparatus for detecting foreign particles adhered on a substrate having a circuit pattern such as a photomask or reticle, comprising:

an inspection stage having a stage for loading and moving the above substrate and a drive control system thereof;

an illumination system for illuminating the above circuit pattern slantwise;

a means for condensing scattered light and diffracted light generated at the same location of the above circuit pattern by illumination of the above illumination system;

a detection optical system for imaging the above circuit pattern on the basis of the above condensed light;

a detector installed on the imaging plane by the above detection optical system;

a circuit for correcting detected values of the above detector according to uneven illumination by the above illumination system;

a circuit for obtaining an added value of the detected values of 2 by 2 pixels among the above detected values;

a circuit for obtaining the maximum value of four added values which are shifted pixel by pixel in the four directions around each detector pixel; and a signal processor for processing data from the above foreign particles on the basis of the above obtained signal.

Next, operations of the characteristics of the present invention will be described.

According to the conventional literature, for example, Wolf, "Principle of Optics", pp 647 to 664, when small particles are almost equal to the wave length of illumination light in size, scattered light from foreign particles is not uniform and distributed sharply.

The present invention is based on the fact that the aforementioned increase in missing of foreign particles is caused by a distribution of scattered light from those small particles.

This is because not only the numerical aperture (NA) of the detection optical system has not been referred to but also it is considered that foreign particles can be detected even if the detection optical system cannot resolve them. Since scattered light from small particles has irregular directivity as shown in the above literature, however, they may not be detected by a detection optical system with a small numerical aperture. Therefore, it can be considered that it results in missing of foreign particles.

The ideology of the present invention shows that a detection optical system having the resolution of the prior art may detect small foreign particles but cannot detect them stably. It is ascertained that also to accomplish a target of "detection of foreign particles", a resolution for resolving the size of foreign particles to be detected or so is necessary. The process of investigation will be described hereunder.

The physics of light scattering is extremely complicated. A simplest problem such that a plane wave is irradiated to a single ball floating in the air was analyzed first by Gustav Mie in 1908.

The solution which is known as a Mie's theory is a summing up series of mathematic function which is called spherical harmonics. It will not be referred to here because it is beside the subject of the present invention.

A particle such as a latex ball scatters light of an incident beam by a combination of processes of reflection, refraction, absorption, and diffraction. FIG. 21 shows the intensity of scattered light from ball like foreign particles.

FIG. 21 expresses the theoretical value of scattered light intensity from the foreign particles by a dimensionless number of $\pi D/\lambda$ using a wave length of of a laser beam and a foreign particle diameter of D and the theoretical value of Mie scattering is modified to that of a particle adhered onto a substrate as an application example of the present invention.

The horizontal axis indicates a dimensionless number using a wave length of $\lambda$ of the detected light (for example, 550 nm) and a detected foreign particle diameter of d.

The area wherein the value of $\pi d/\lambda$ is less than about 4 (foreign particles smaller than $d=0.7$ $\mu$m when $\lambda=550$ nm) is called particularly a Rayleigh scattering area, and the scattered light from foreign particles suddenly decreases in inverse proportion to the diameter to the 6th power. Therefore, detection of foreign particles in this area requires great care to the detector sensitivity.

In the area wherein the value of $\pi d/\lambda$ is larger than about 4, the scattered light scatters with directivity according to the diffraction theory.

The situation is shown in FIGS. 14A-B.

FIGS. 14A-B are drawings showing that scattered light from foreign particles is detected by using a high NA optical system according to the present invention. Since the scattered light from the foreign particles has a distribution, it is necessary to determine the numerical aperture (NA) of the detector in consideration of the scattered light distribution when detecting foreign particles in this area.

FIG. 22 is a schematic view showing the direction of diffracted light from a foreign particle.

FIG. 22 shows the direction of diffracted light when a laser beam 2221 is irradiated to a foreign particle 70 on a reticle 6. The diffracted light is followed by 0dimensional diffracted light 2222, 1-dimensional diffracted light 2223, 2-dimensional diffracted light at an angle of $\theta$, . . . .

The 0-dimensional diffracted light 2222 is a positive reflected light of the laser beam 2221 and detection of scattered light from foreign particles means detection of one-dimensional or higher-dimensional diffracted light.

The above $\theta$ is obtained from the diffracted light equation:

$$d_0 \cdot \sin\theta = \lambda$$

wherein, $d_0$ is defined variously such as diameter, width, length, or mean value of diameter. The following argument is held regardless of the value of $d_0$.

Therefore, any of the above definitions will not affect the result.

Therefore, it is assumed here that $d_0=d$ or $d_0$ indicates a foreign particle diameter.

The necessary numerical aperture (NA) of the detection optical system is obtained under the most severe condition $\pi d/\lambda=4$.

$\pi \cdot d/\lambda=4$  $d/\lambda=1.27$  $\lambda/d=0.79$

From $\sin\theta=\lambda/d$: $\theta=\sin^{-1}(0.79)=52°$

This means that the maximum gap of diffracted light is 52°. When a detection optical system with an aperture of more than 52° is used, therefore, at lowest one-dimensional diffracted light can be detected, resulting in no missing of foreign particles.

FIG. 23 is a schematic view showing the definition of the numerical aperture (NA) of an optical system.

In FIG. 23, the numerical aperture (NA) of an object lens 41 of the detector system is obtained from NA=sin (θ/2) (n: a refractive index of the optical path, n≃1 in the air).NA=1.sin (52°/2)=0.44

Therefore, scattered light from foreign particles can be detected without missing by a detector system having NA larger than about 0.44.

In this case, as the NA increases, the detection capability also increases and foreign particles in the Rayleigh area can be detected more conveniently. When NA is close to 0.4 even if it is less than 0.44 inversely, foreign particles can be detected practically because diffracted light has a certain width. When NA is more than 0.5 inversely, scattered light from the circuit pattern enters into the detector system for the reason which will be described later and the request for detecting only scattered light from foreign particles is turned down, causing a reduction in advantages of increasing NA especially. Therefore, NA ranging from 0.4 to 0.6 or so is practically suited.

Next, detection of foreign particles in the Rayleigh area will be described.

As mentioned above, a detection optical system having the resolution of the prior art may detect small foreign particles but cannot detect them stably. To accomplish a target of "detection of foreign particles", a resolution for resolving the size of foreign particles to be detected or so is necessary.

The present invention has a detection optical system having the numerical aperture (NA) for resolving foreign particles to be detected or so. Concretely, NA is calculated from Equation (1) indicated below.

$$d = 0.6 (\lambda/NA) \quad (1)$$

An optical system having a value close to this NA is desirable. In the above equation, a symbol d indicates the size of foreign particles to be detected, λ the wave length of illumination light, and NA the numerical aperture. When NA of the detector system cannot be set so as to satisfy Equation (1), it is necessary to shorten λ of the illumination system so as to satisfy the equation (1).

In a conventional detection optical system for foreign particle inspection, it is not considered that the resolution for resolving foreign particles is necessary. The present invention is based on a new concept that a detection optical system for resolving foreign particles as shown in Equation (1) is necessary.

However, the coefficient of Equation (1) is not required to be as large as the value for calculating the general resolution such as 0.6. The experiment conducted by the inventor for the present invention shows that when NA ranges from 0.24 to 0.6, the necessary foreign particle detecting precision is obtained.

Next, the reason will be described. FIG. 24 is a chart showing the scattering cross section, which is proportional to the scattered light intensity from foreign particles, vs the foreign particle diameter.

In FIG. 24, the horizontal axis represents the foreign particle diameter and the vertical axis represents the scattering cross section. This scattering cross section is in proportion to the scattered light generated from foreign particles and can be obtained from the Mie's scattering theory. The interpretation means that when generated scattered light is observed, it is observed as if it were scattered light generated from the foreign particles shown by the solid line in the drawing. The drawing also shows the geometrical cross section using a dashed line. The drawing shows that when observed using scattered light, the observed foreign particle size is larger than the actual size. (This is just the reason why foreign particles are inspected by scattered light.) FIG. 24 shows that the ratio is 3 to 6 times or so in area ratio and hence $\sqrt{3}$ to $\sqrt{6}$ times in diameter.

In this case, Equation (1) is expressed as follows:

$$\begin{aligned}d &= (0.6/\sqrt{3} \text{ to } \sqrt{6}) \cdot (\lambda/NA) \\ &= (0.24 \text{ to } 0.35) \cdot (\lambda/NA)\end{aligned} \quad (1')$$

The previous experiment result can be well explained by this equation.

It is said that in the case of foreign particle inspection on a reticle, the foreign particle size d to be detected is about ¼ of the minimum pattern size on the reticle. Therefore, when the minimum size of the pattern on the reticle is 2.5 μm (in the case of 5:1 reduction transfer, 0.5 μm on a wafer which is equivalent to 16 MDRAM), the foreign particle size is 0.6 μm or when the minimum size on the reticle is 1.5 μm (equivalent to 64 MDRAM), the foreign particle size is 0.4 μm.

Therefore, to detect 0.4 μm foreign particles by a detection optical system with NA=0.4 which is obtained by the previous investigation, a light source with a wave length shorter than λ=660 nm to 460 nm is necessary from the following equation which is derived from Equation (1').

$$\lambda = d \cdot NA/(0.35 \text{ to } 0.24) \quad (2)$$

Next, selection of a wave length which is suited to foreign particle inspection on a sample such as a reticle with circuit patterns formed thereon in this wave length range will be investigated. The principle for optically separating and detecting foreign particles from circuit patterns, which is necessary for wave length selection, will be explained first.

The present invention is based on the fact that a reticle circuit pattern comprises straight lines in the three directions such as longitudinal, transverse, and slant and the transposition parts (hereinafter called circuit pattern corners) of the above straight lines. When the above circuit pattern is irradiated by a directional laser beam slantwise at an incident angle of i (i<90°), it is well known that a Fourier transformed image of scattered light from the straight lines of the circuit pattern is condensed at a specific location on the Fourier tranform plane into a narrow straight line instead of the circuit pattern location in the illumination field and the scattered light from foreign particles is not biased to a specific location on the Fourier transform plane.

Therefore, the present invention is based on the principle that a linear shaped shutter (called a spatial filter) is arranged at a specific location on the Fourier transform plane so as to shield scattered light from the straight lines of the circuit pattern and only scattered light from foreign particles can be detected. However, scattered light from the above circuit pattern corners and the fine structure section formed by the continued corners cannot be shielded fully. Therefore, when 10 by 20 μm² detection pixels are used for detection as conventional (shown in FIG. 4(B)), scattered light from a plurality of pattern corners enters into the pixels and it is impossible to detect only foreign particles.

In the present invention, therefore, each pixel of the detector is highly resolved to 2 by 2 μm² (shown in FIG. 4(C)) so as to eliminate the effect of the circuit pattern inasmuch as is possible and 0.5-μm foreign particles can be detected. Therefore, each pixel of the detector is set to 2 by 2 μm² for the reason which will be described later. However, there is no need to set it to 2 by 2 μm².

It is desirable that the pixel size in this case is smaller than the smallest pattern size L on the reticle. Therefore, it is desirable that pixels with a size smaller than about $0.8 \times 5 = 4$ μm are used for detection for a reticle when 0.8-μm process LSIs are exposed by a stepper with a reduction rate of 1/5 or pixels with a size smaller than about $0.5 \times 5 = 2.5$ μm are used for 0.5-μm process LSIs.

The pixel size may be larger or smaller insofar as it can sufficiently minimize the effect of the pattern corners.

Concretely, the pixel size which is similar to the minimum pattern size on the reticle which is to be detected is desirable. When the pixel size is similar to this minimum pattern size, scattered light from at most one corner enters into a pixel of the detector and the experiment shown in FIG. 10 shows that this value is large enough.

Concretely furthermore, for a 64 MDRAM reticle with a minimum size of about 1.5 μm, a pixel size of 1 to 2 μm or so is desirable.

The foregoing and other objects, advantages, manner of operation and novel features of the present invention will be understood from the following detailed description when read in connection with the accompanying drawings.

BRIEF DESCRIPTION OF THE DRAWINGS

FIG. 12 is a drawing for explaining problems of the prior art;

FIG. 16 is a columnar graph showing the number of detected foreign particles vs the size of detected foreign particles by the present invention and the prior art;

DETAILED DESCRIPTION OF THE PREFERRED EMBODIMENTS

Firstly, the structure of an embodiment of the present invention will be described with reference to FIGS. 1 to 3(A) and 3(B).

Figure 1:
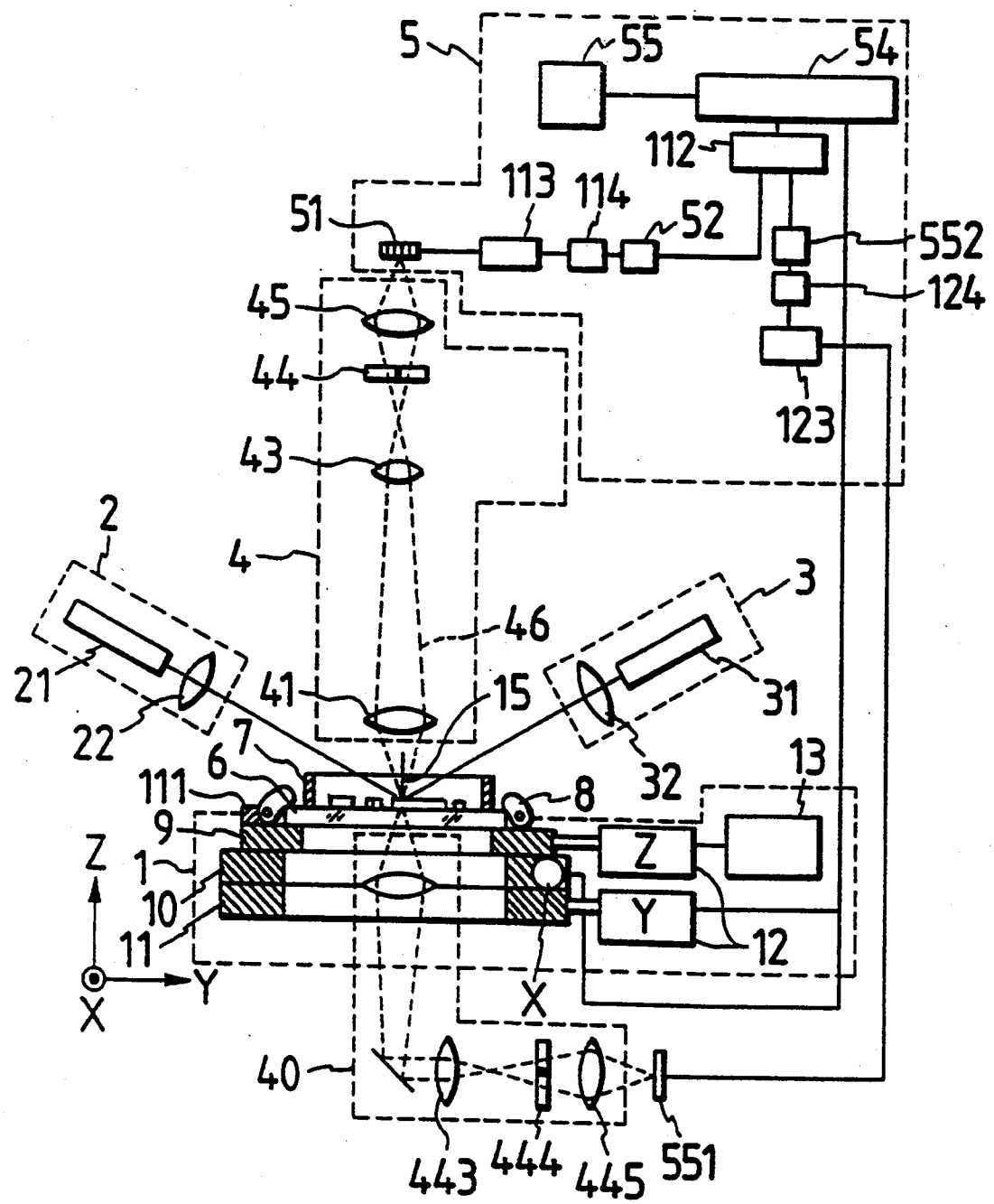
FIG. 1 is a block diagram showing the structure of a foreign particle inspection apparatus according to an embodiment of the present invention.
Figure 2:
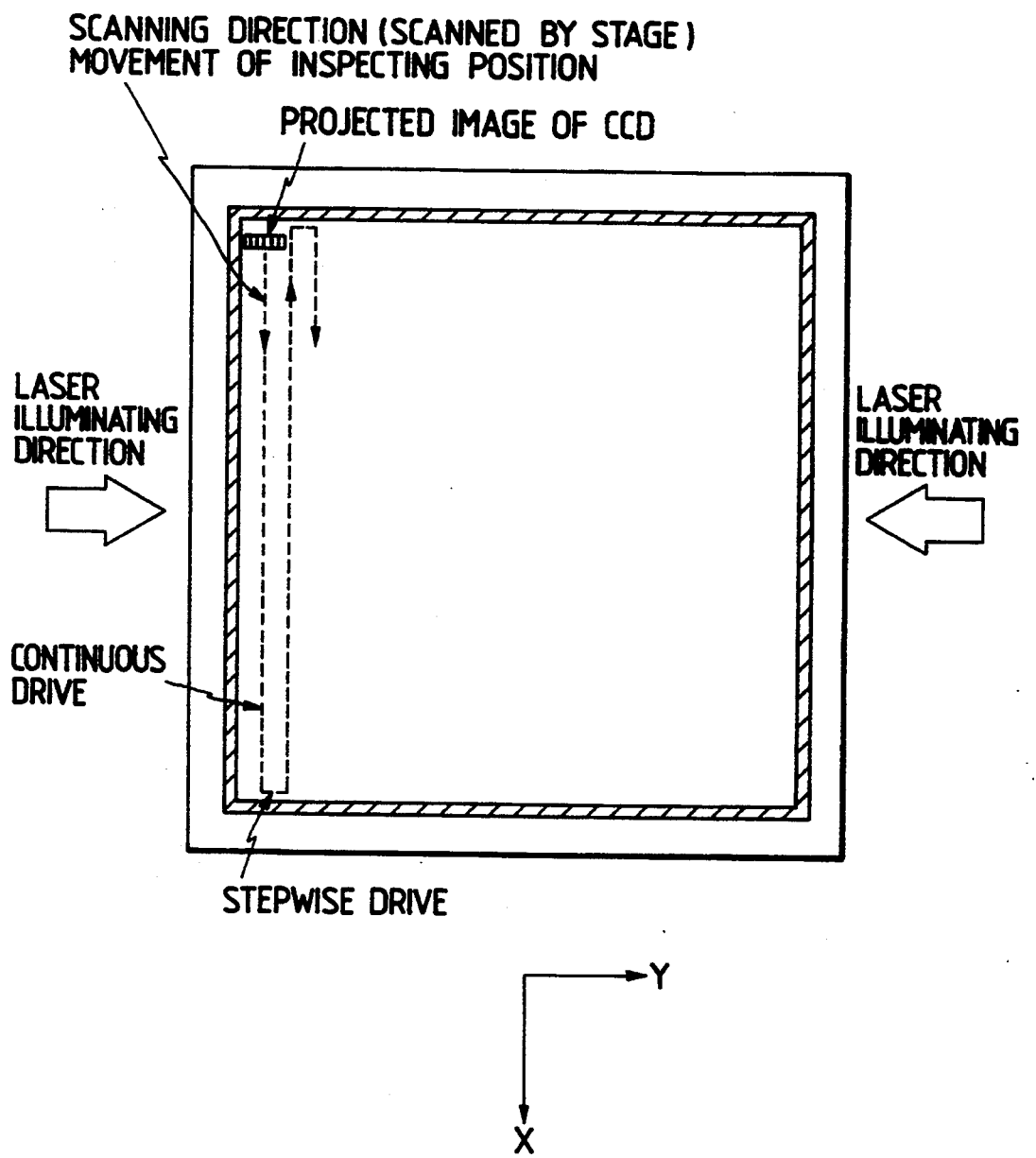
FIG. 2 is a plan view showing the reticle inspection status of the equipment shown in FIG. 1.
Figure 3A:
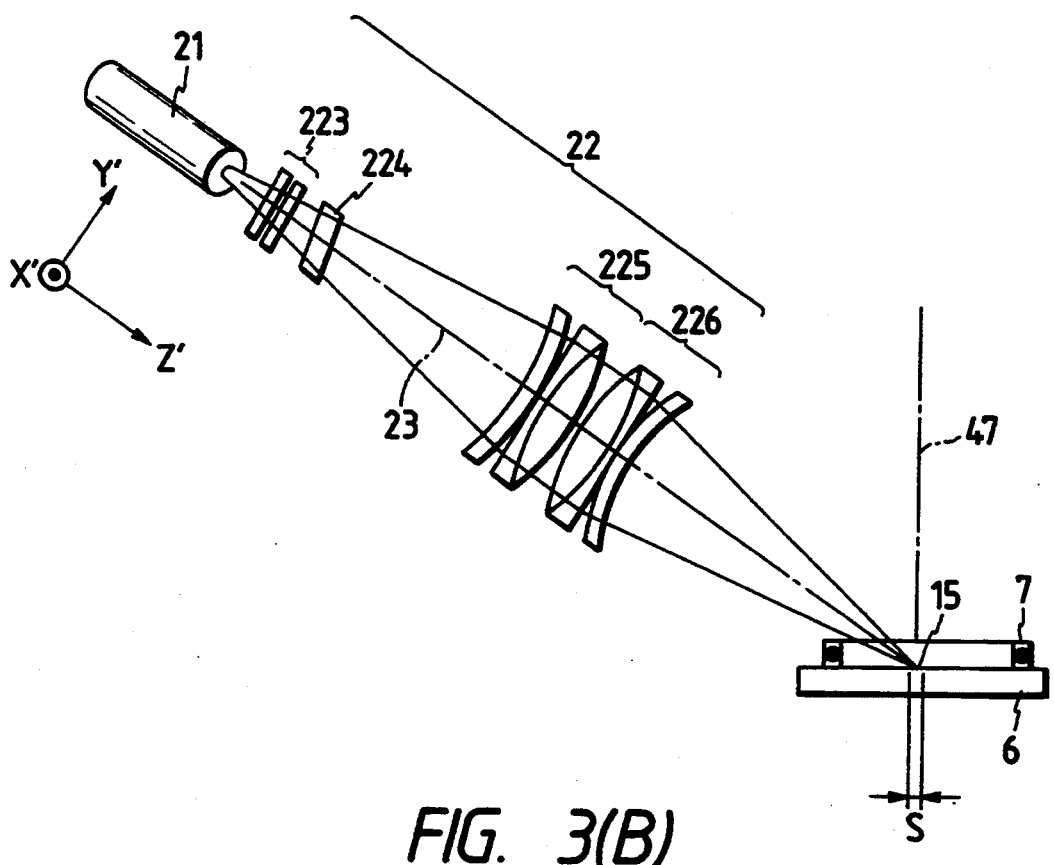
FIGS. 3(A) and 3(B) are diagrams for explaining structure examples of the illumination system of the equipment shown in FIG. 1.
Figure 3B:
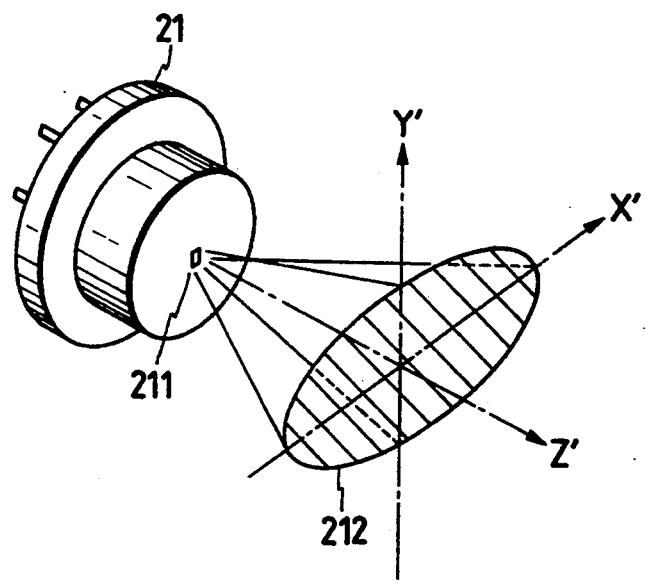

FIG. 1 is a block diagram showing the structure of a foreign particle inspection apparatus according to an embodiment of the present invention, FIG. 2 is a plan view showing the reticle inspection status of the equipment shown in FIG. 1, and FIGS. 3(A) and 3(B) are diagrams for explaining structure examples of the illumination system of the equipment shown in FIG. 1.

In FIG. 1, numeral 1 indicates an inspection stage unit which comprises a Z stage 9 for fixing a reticle 6 having a pellicle 7 to the top with a fixing means 8 and moving it in the Z direction, an X stage 10 for moving the reticle 6 in the X direction via the Z stage 9, a Y stage 11 for moving the reticle 6 in the Y direction in the same way, a stage drive system 12 for driving the Z stage 9, X stage 10, and Y stage 11, and a focal position detection control system 13 for detecting the position of the reticle 6 in the Z direction. Each stage is controlled so that the focus can be adjusted always with necessary accuracy during inspection of the reticle 6.

The X stage 10 and the Y stage 11 are scanned in the direction of the dashed line shown in FIG. 2 and the scanning speed can be set optionally. When, for example, the X stage 10 is formed to perform a periodical motion consisting of a uniform acceleration time of about 0.2 seconds, a uniform motion of 4.0 seconds, a uniform deceleration time of 0.2 seconds, and a stop time of about 0.2 seconds at a one-half period, at a maximum speed of about 25 mm/second, and at an amplitude of 105 mm and the Y stage 11 is structured so as to move the reticle 6 in the Y direction stepwisely by 0.5 mm each time in synchronization with the uniform acceleration time and uniform deceleration time of the X stage 10, assuming that the reticle is moved 200 times during the time of one inspection, it is possible to move the reticle by 100 mm for about 960 seconds. Therefore, a 100 mm square area can be scanned for about 960 seconds.

Further, the focal point detection control system 13 may use an air micrometer, or may detect the position by the laser interference method, or may project a fringe pattern to detect the contrast. The directions of the axes X, Y, and Z are as shown in the drawing.

In FIG. 1, numeral 2 indicates a first illumination system and 3 a second illumination system, and the two are independent of each other and comprise the same types of components. Numerals 21 and 31 indicate laser beam sources. The wave lengths of the laser beams in this example are different from each other such that the wave length $\lambda_1$ of the laser beam source 21 is, for example, 514.5 nm and the wave length $\lambda_2$ of the laser beam source 31 is, for example, 532 nm. However, the wave lengths of both laser beams may be generally the same. Numerals 22 and 32 indicate focusing lenses which condense the fluxes of light emitted from the laser beam sources 21 and 31 and irradiate them onto the circuit pattern of the reticle 6. In this case, it is required the incident angles i of both fluxes of light to the circuit pattern are more than about 30° so as to avoid an object lens 41 of a detection optical system 4 which will be described later and when the sample to be inspected is the reticle 6 with the pellicle 7 mounted thereon, the incident angles i are less than about 80° to avoid the pellicle 7. Therefore, 30°<i<80° or so.

Detailed structure examples of the first illumination system 2 and the second illumination system 3 mentioned above will be explained with reference to FIGS. 3(A) and 3(B). FIGS. 3(A) and 3(B) show structure examples of the first illumination system 2 (structure examples of the second illumination system 3 are omitted due to the same structure). The numerals shown in the drawings which are the same as those shown in FIG. 1 indicate the same parts.

In FIG. 3(A), numeral 223 indicates a concave lens, 224 a cylindrical lens, 225 a collimator lens, and 226 a focusing lens. The lenses 223 to 226 constitute the focusing lens 22. The laser beam source 21 is arranged so that it has a linearly polarized laser beam (this status is called S polarization) having a magnetic field vector in the Y' direction. The reason of use of S polarization is that when the incident angle i is, for example, about 60°, the reflectance on the glass substrate is higher than that in the case of P polarization by about 5 times (for example, H. Kubota, Applied Optics (Iwanami Zensho), p. 148) and smaller foreign particles can be detected.

FIG. 3(B) is a perspective view showing the status of the flux of light emitted from the laser beam source 21 which is sectioned at an optional Z' position in parallel with the X'- Y' plane.

Numeral 21 indicates a laser beam source using a semiconductor laser, which has an emission point 211 of a rectangle of about 1 μm max. in width (X' direction) by several μm to several tens μm in length (Y' direction). A laser beam emitted from the emission point 211 diffracts at an angle which is wide in the width (X') direction by a diffraction phenomenon at the emission point 211 so as to form an elliptical flux of light 212 as shown in FIG. 3(B). Since the laser beam source 21 uses a semiconductor laser, it generally has a linearly polarized laser beam having a magnetic field vector in the Y direction. Further to collimate the laser beam small into a detection field 15 shown in FIG. 3(A), it is necessary to irradiate the laser beam to the convex lens 223 at an angle wider than the laser beam source 21. By this reason, a laser beam whose longitudinal direction is the Y' direction shown in FIG. 3(A) is formed by the cylindrical lens 224.

To increase the illumination intensity of the first illumination system 2 and the second illumination system 3, the numerical aperture (NA) of the condensing system is set to about 0.1 and the laser beam is collimated to about 10 μm. This collimation shortens the focal depth to about 30 μm and the laser beam cannot be focused over the entire area S (500 μm) of the detection field 15 shown in FIG. 3(A). However, this embodiment has a countermeasure for it that the cylindrical lens 224 leans round the X' axis shown in FIG. 3(A) (FIG. 3(A) shows the status when the lens leans) and hence the laser beam can be focused over the entire area S of the detection field 15 even when the incident angle i is, for example, 60°. Furthermore, when one-dimensional solid imaging devices are used as detectors 51 and 551 of a signal processor system 5 which will be described later, even if the inspection area of the detection field 15 is made linear in the same way as with the detectors 51 and 551, it is possible to illuminate the above linear inspection area at a high illumination intensity and at a uniform distribution.

Furthermore, when the cylindrical lens 224 leans round the Y' axis in addition to the X' axis shown in FIG. 3(A), even if the laser beam is irradiated in an optional direction at an incident angle i of 60°, it is possible to illuminate the entire area S of the detection field 15 linearly at a high illumination intensity and at a uniform distribution.

In FIG. 1, numeral 4 indicates a detection optical system which comprises an object lens 41 opposite to the reticle 6, a field lens 43 installed near the imaging position of the object lens 41, a mirror (not shown in the drawing) for separating the wave length of the flux of light condensed by the field lens 43, spatial filters 44 and 444 having a linear shutter section installed at the Fourier transform position against the detection field 15 of the reticle 6 and a transmission section outside the shutter section, and imaging lenses 45 and 445. Furthermore, the detection field 15 on the reticle 6 is structured so that images are formed on detectors 51 and 551 of a signal processor system 5 which will be described later. The field lens 43 is used to image the focal position 4 above the object lens 41 on the spatial filters 44 and 444.

In FIG. 1, numeral 5 indicates a signal processor system which comprises the aforementioned detectors 51 and 551, first and second binarizers 52 and 552 for binarizing outputs of the above detectors 51 and 551, a microcomputer 54, and a display means 55.

The detectors 51 and 551 are formed, for example, by charge coupled type one-dimensional solid imaging devices and detects signals from the circuit pattern on the reticle 6 by scanning the X stage 10. When foreign particles exist on the reticle 6 in this case, the signal level to be inputted and the light intensity increase. Therefore, the detectors 51 and 551 are formed so that outputs thereof also increase. When one-dimensional solid imaging devices are used for the detectors 51 and 551 as mentioned above, there is an advantage that the detection field can be spread with the resolution maintained. However, there are no restrictions on it. Two-dimensional elements or single elements may be used.

In the binarizers 52 and 552, binary threshold values are set beforehand and when output values more than the reflected light intensity equivalent to foreign particles in the required size to be detected which are outputted from the detectors 51 and 551 are inputted, the logical level "1" is outputted.

Shading correction circuits 113 and 123 and 4-pixel addition circuits 114 and 124 will be described later. A block processor 112 reads signals from the binarizers 52 and 552 and prevents double counting of two signals, which will be described later.

When the block processor 112 outputs the processing level "1", the microcomputer 54 judges that there is a foreign particle, and stores the position information of the X stage 10 and the Y stage 11, and when the detectors 51 and 551 are not single elements, the foreign particle position information calculated from the pixel position in the elements, and the detected output values of the detectors 51 and 551 as foreign particle data and outputs the results to the display means 55.

Next, the operation of the inspection apparatus will be explained with reference to FIGS. 4A-D to 10 and 36.

Figure 4B:
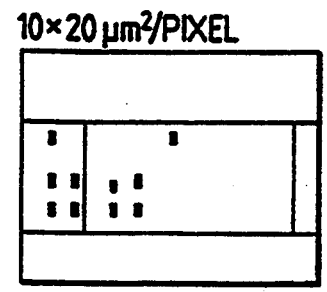
FIGS. 4(A)-(D) are diagrams for explaining the reticle inspection status according to the present invention.
Figure 4A:
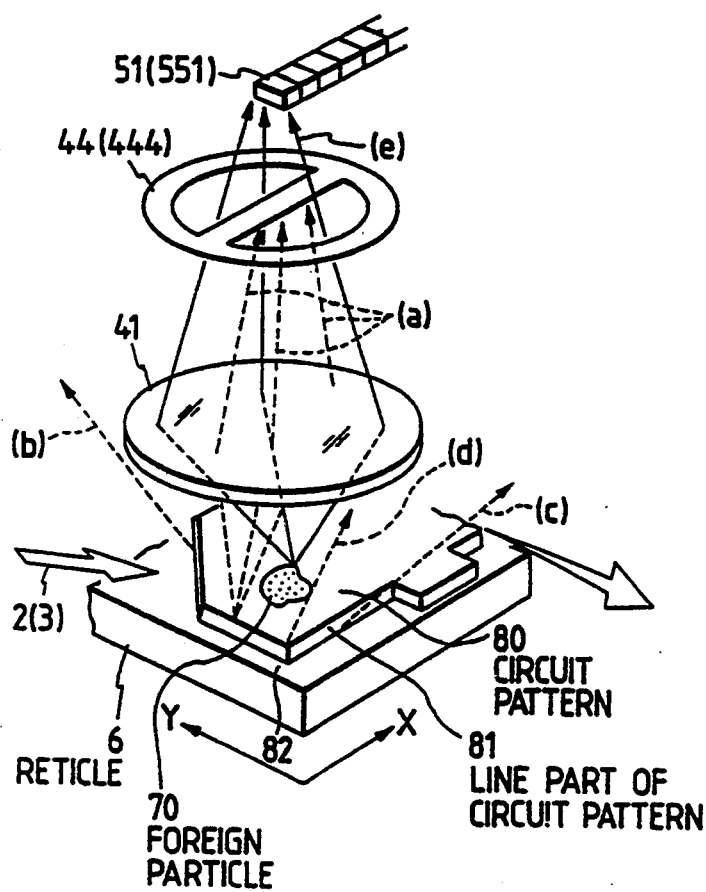
Figure 4C:
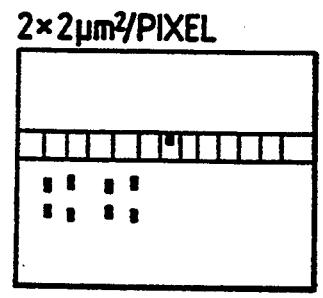
Figure 4D:
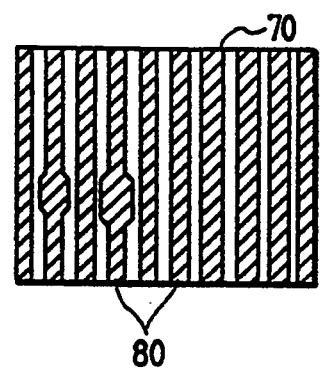
Figure 5:
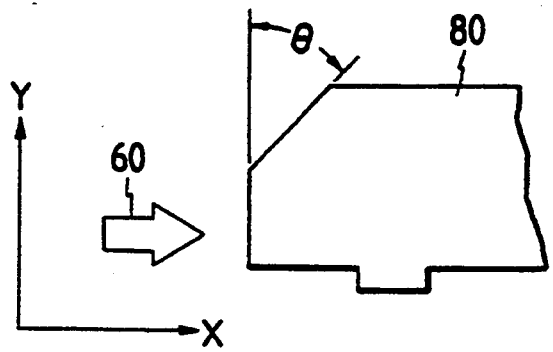
FIG. 5 is a plan view for explaining an angle pattern of a circuit pattern according to the present invention.
Figure 6A:
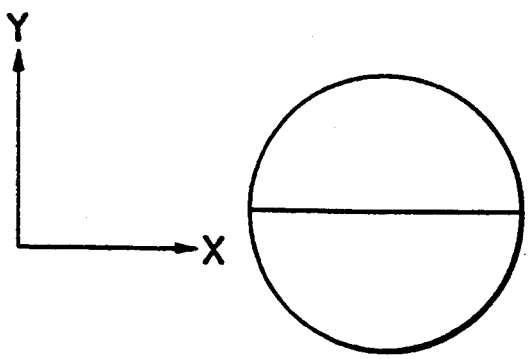
FIGS. 6A-C are diagrams for explaining the distribution status of scattered light and diffracted light on a Fourier transform plane according to the present invention.
Figure 6B:
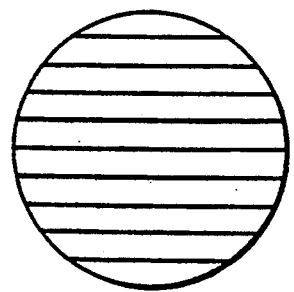
Figure 6C:
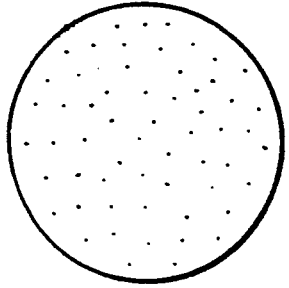
Figure 7A:
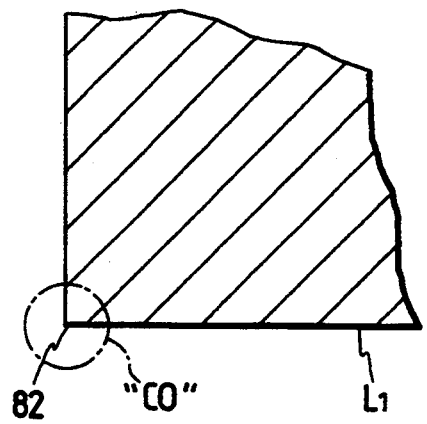
FIGS. 7(A), 7(B) is an enlarged drawing of corners of a circuit pattern.
Figure 7B:
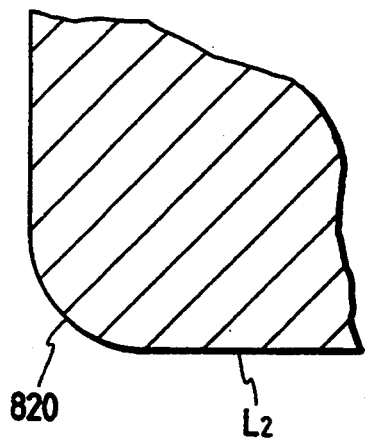
Figure 8:
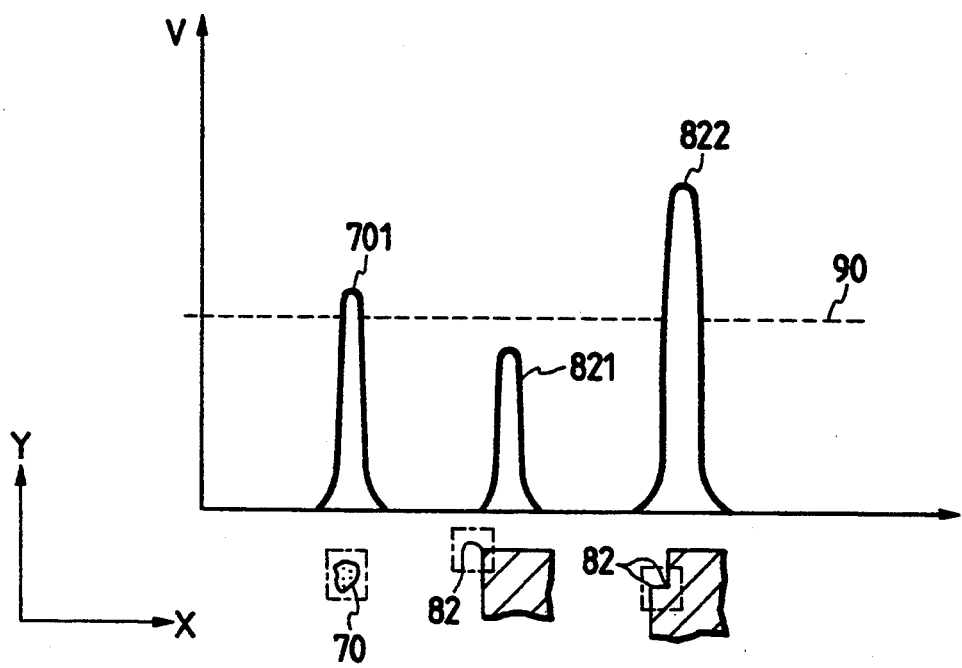
FIG. 8 is a drawing for explaining the relation between the scattered light detection output value from a foreign particle and the detection output value from a circuit pattern.
Figure 9:
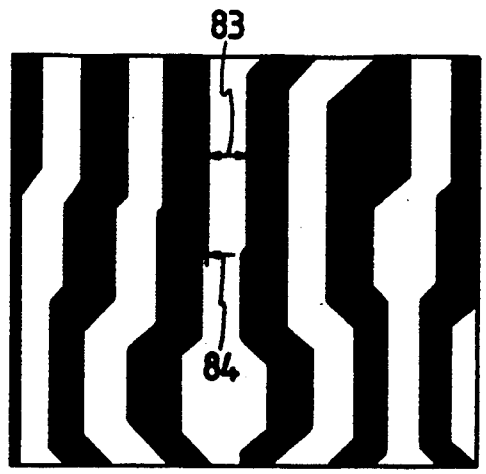
FIG. 9 is an enlarged drawing showing a circuit pattern having a fine structure pattern.
Figure 10:
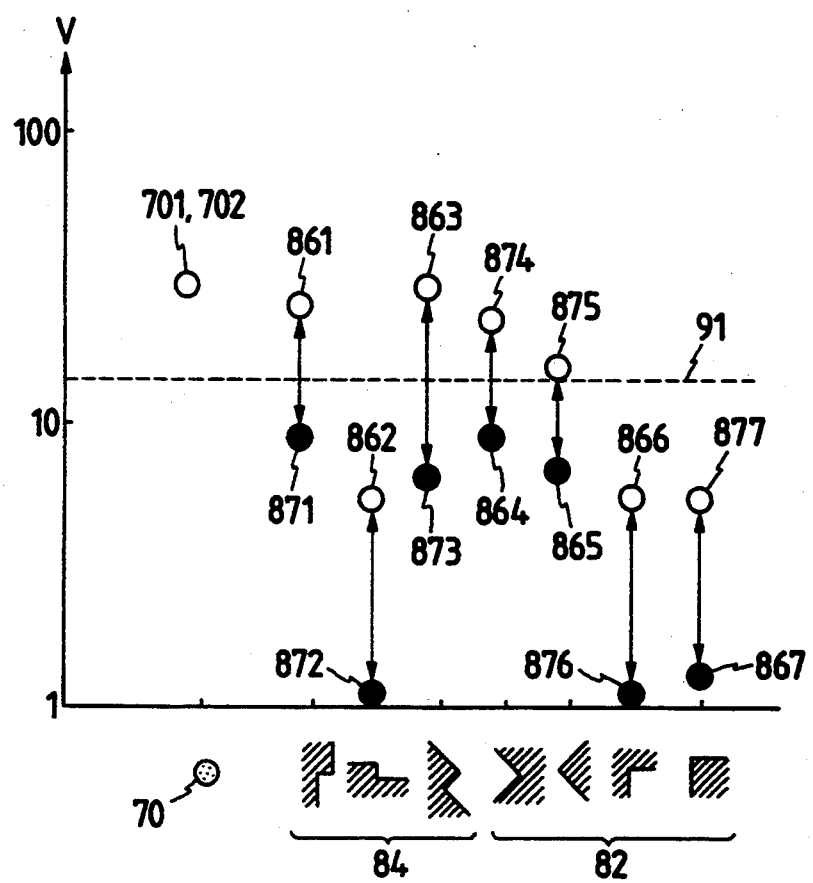
FIG. 10 is a drawing showing the output value level of detected signals detected from foreign particles and circuit pattern corners.

FIG. 4A-D are diagrams for explaining the reticle inspection status according to the present invention, FIG. 5 is a plan view for explaining an angle pattern of a circuit pattern according to the present invention, FIG. 6A-C are diagrams for explaining the distribution status of scattered light and diffracted light on a Fourier transform plane according to the present invention, FIG. 7 is an enlarged drawing of corners of a circuit pattern, FIG. 8 is a drawing for explaining the relation between the scattered light detection output value from a foreign particle and the detection output value from a circuit pattern, FIG. 9 is an enlarged drawing showing a circuit pattern having a fine structure pattern, and FIG. 10 is a drawing showing the output value level of detected signals detected from foreign particles and circuit pattern corners. The numerals shown in the drawings which are the same as those shown in FIG. 1 indicate the same parts.

In FIG. 4(A), numeral 70 indicates a foreign particle on the reticle 6 which is fixed on the Z stage 9 by the fixing means, 81 a line part of a circuit pattern 80, and 82 a corner of the circuit pattern 80.

When the reticle 6 according to the substrate sample is illuminated by the first illumination system 2 or the second illumination system 3 slantwise and scattered light generated is condensed by the object lens 41, diffracted light of the angle pattern (hereinafter called the 0° pattern) when the angle $\theta$ which is defined by the location relationship between the circuit pattern 80 on the reticle 6 shown in FIG. 5 and a projected image 60 onto the reticle 6 of the illumination system 2 or 3 is 0° is displayed linearly on the Fourier transform plane of the object lens 41 as shown in FIG. 6A representing defracted light (a) of FIG. 4A. The type of angle $\theta$ of the above circuit pattern 80 is limited to 0°, 45°, and 90°. Diffracted lights (b) and (c) from the 45° and 90° patterns do not enter the eye of the object lens 41 as shown in FIG. 4 and the detection is not affected.

Scattered light from the foreign particle 70 is not directive and spread all over the Fourier transform plane as shown in FIG. 6C representing defracted light (e) of FIG. 4A. Therefore, by arranging spatial filters 44 and 444 having a linear shutter section on the Fourier transform plane and a transmission section outside the shutter section so as to shield diffracted light (a) from the 0° pattern shown in FIG. 4(A), it is possible to discriminate and detect the foreign particle 70 from the circuit pattern 80.

This structure realizes a high NA detection optical system first and when the NA is set to 0.5, the aperture area can be set to about 20 times of that of a low NA detection optical system.

Scattered light from the circuit pattern corner (see FIG. 4(D)) cannot be shielded fully by a linear shaped spatial filter. Therefore, when 10 by 20 $\mu m^2$ detection pixels are used for detection as conventional (see FIG. 4(B)), scattered light from a plurality of pattern corners enters into the 4 pixels and it is impossible to detect only foreign particle.

In the present invention, therefore, each pixel of the detector is highly resolved to 2 by 2 $\mu m^2$ (see FIG. 4(C)) so as to eliminate the effect of the circuit pattern inasmuch as is possible and 0.5-$\mu m$ foreign particles can be detected. Therefore, each pixel of the detector is set to 2 by 2 $\mu m^2$ for the reason which will be described later. However, there is no need to set it to 2 by 2 $\mu m^2$.

It is desirable that the pixel size in this case is smaller than the smallest pattern size L on the reticle.

Therefore, it is desirable that pixels with a size smaller than about $0.8 \times 5 = 4$ $\mu m$ are used for detection for a reticle when 0.8-$\mu m$ process LSIs are exposed by a stepper with a reduction rate of 1/5 or pixels with a size smaller than about 0.5×5=2.5 μm are used for 0.5-μm process LSIs.

The pixel size may be larger or smaller insofar as it can sufficiently minimize the effect of the pattern corners.

Concretely, the pixel size which is similar to the minimum pattern size on the reticle which is to be detected is desirable. When the pixel size is similar to this minimum pattern size, scattered light from at most one corner enters into a pixel of the detector and the experiment shown in FIG. 10 shows that this value is large enough.

Concretely furthermore, for a 64 MDRAM reticle with a minimum size of about 1.5 μm, a pixel size of 1 to 2 μm or so is desirable.

The above contents will be explained once again with reference to FIGS. 7A–B. A corner section 82 formed in the transposition part of the circuit pattern 80 shown in FIG. 7(A) comprises a corner 820 with continuous angles as shown in FIG. 7(B) wherein the above section CO is shown microscopically and diffracted light (d) from the corner section 82 also has a tendency to spread on the Fourier transform plane and cannot be shielded perfectly by the spatial filters 44 and 444 as shown in FIG. 6B representing defracted light (d) of FIG. 4A. Therefore, when diffracted light from a plurality of corner sections 82 enters into one of the detectors 51 and 551, the output V of the detector 51 or 551 increases and the foreign particle 70 cannot be discriminated and detected.

FIG. 8 shows the status; that is, a detected output value 822 from a plurality of corner sections 82 is higher than a detected output value 821 from a single corner section 82 and when binarized at the level of a dashed line 90 shown in the drawing, a detected output value 701 from the foreign particle 70 cannot be separated and detected.

As a countermeasure for the defect described in FIG. 8, in the present invention, the detection field 15 on the reticle 6 is structured so that images are formed on the detectors 51 and 551 via the object lens 41 and the imaging lenses 45 and 445 and the detection field 15 on the reticle 6 is set to an optional size (for example, 2 μm by 2 μm) by selecting the size of the detectors 51 and 551 and the imaging magnification so as to prevent diffracted light from a plurality of corner sections 82 from entering into the detectors 51 and 551 simultaneously though the detection optical system 4 is simple.

Although foreign particles with the aforementioned conventional size can be detected, for detection of foreign particles of the order of submicrons, the separation and detection from a part of the corner section 82 may be insufficient depending on the shape of the circuit pattern 80. Furthermore, diffracted light generated from a circuit pattern having a size 84 of the order of microns shown in FIG. 9 which is finer than a size 83 of the normal structure part of the circuit pattern 80 due to high integration of LSIs is more similar to scattered light from the foreign particle 70 in behavior and hence it is further difficult to separate and detect the foreign particle 70 from the circuit pattern.

The present invention has a countermeasure, which will be explained hereunder, for a circuit pattern having the size 84 of the order of microns shown in FIG. 9 so as to detect foreign particles.

FIG. 10 is a diagram for explaining it. In the drawing, numerals 701 and 702 indicate detected output values of scattered light from the small foreign particle 70 of the order of submicrons, 864, 874, 865, 875, 866, 876, 867, and 877 detected output values of diffracted light from all the corner sections 82 formed by circuit patterns of 0°, 45°, and 90°, and 861, 871, 862, 872, 863, and 873 detected output values of diffracted light from a fine structure circuit pattern having the size 84 of the order of submicrons. Among them, numerals 701, 861, 862, 863, 864, 865, 866, and 867 indicate detected output values by the first illumination system 2 and 702, 871, 872, 873, 874, 875, 876, and 877 detected output values by the second illumination system 3.

For example, numerals 861 ⟵⟶ 871 indicate detected output values for each illumination system at the same position of the circuit pattern; that is, 861 indicates the value by the first illumination system 2 and 871 the value by the second illumination system 3. As shown in the drawing, the detected output value of scattered light from the foreign particle 70 in the illumination direction varies little compared with that from the circuit pattern. A dashed line 91 shown in the drawing indicates the threshold value of detected output values.

FIG. 10 shows that the output of diffracted light from the same circuit pattern greatly varies with the illumination direction and when the reticle 6 is illuminated in two opposite slant directions which are shifted in a 180° arc, the output value of the diffracted light in one of the directions is always smaller than the output value from a foreign particle of the order of submicrons as shown by a ● mark in the drawing.

Figure 36:
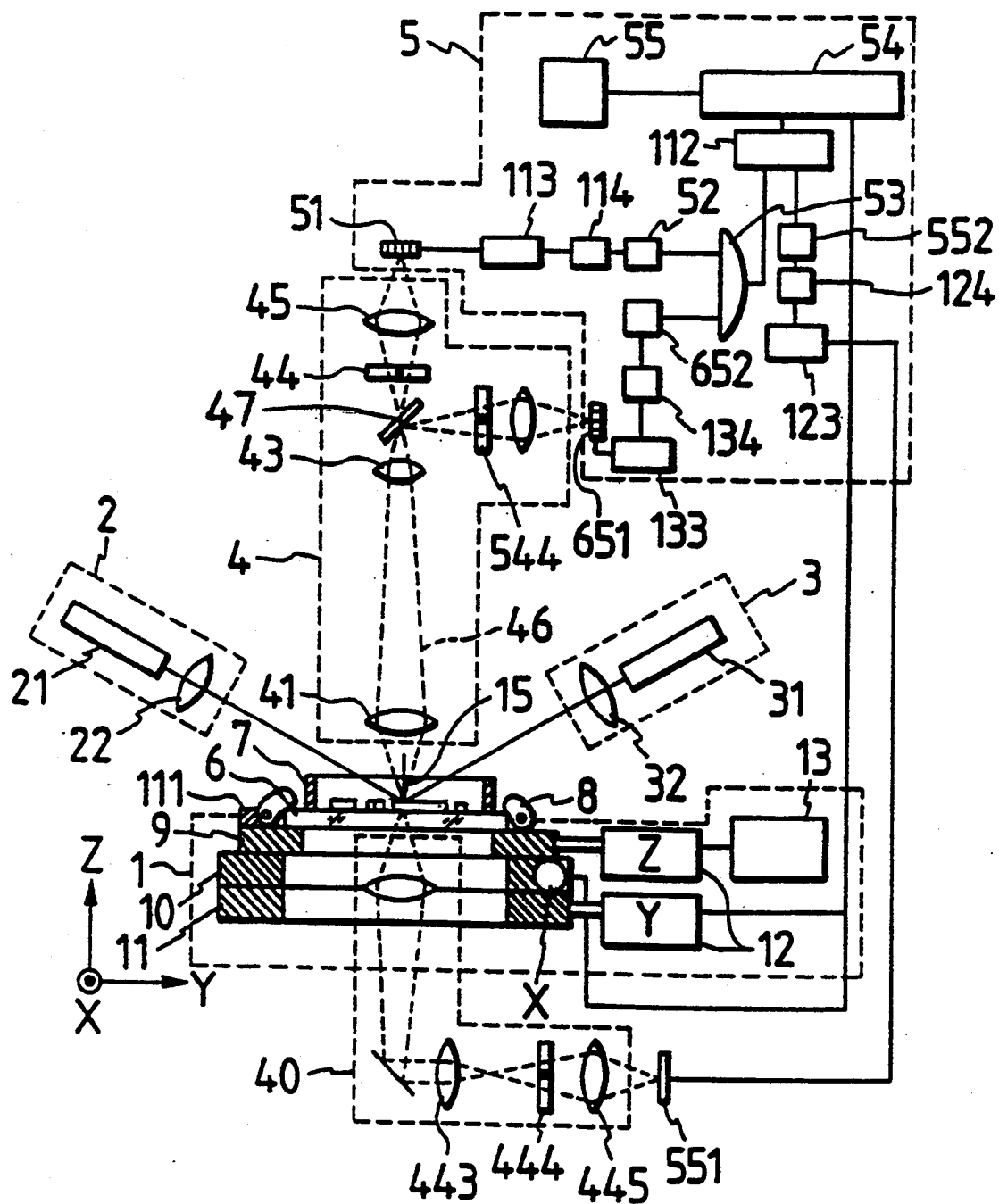
FIG. 36 is a block diagram showing the structure of a foreign particle inspection apparatus according to a further embodiment of the present invention.

FIG. 36 is a block diagram showing the structure of a foreign particle inspection apparatus according to a further embodiment of the present invention. Since the numerals shown in the drawing which are the same as those shown in FIG. 1 indicate the same parts, the description thereof is omitted.

In the apparatus shown in FIG. 36, the aforementioned output values from the same position on the reticle 6 are separated and detected independently by the detectors 51 and 651 via a wave length separation filter 47, and the detected output values which are smaller ones of the values indicated by the aforementioned ● mark are used, and the values are binarized by the binarizers 52 and 652, and the values are ANDed by an AND circuit 53, and only the foreign particle 70 of the order of submicrons is separated and detected from the circuit pattern 80.

As shown in FIG. 10, when the binarizers 52 and 652 are set to the threshold value 91, values more than the threshold value 91 are the detected output values 701 and 702 of the foreign particle 70 and the detected output values 861, 863, 874, and 875 of the circuit pattern. These binary outputs from the circuit pattern are outputted from only one of the binarizers 52 and 552 but not from the AND circuit. Therefore, only the foreign particle 70 can be separated and detected from the circuit pattern. The position information of the X stage 10 and the Y stage 11 at the time of detection, and when the detectors 51 and 651 are not single elements, the position information of the foreign particle 70 calculated from the pixel position in the elements, and the detected output values of the detectors 51 and 651 are stored in the memory managed by the microcomputer 54 as foreign particle data and the stored contents are operated and displayed on the display means 55 such as a CRT.

Figure 13:
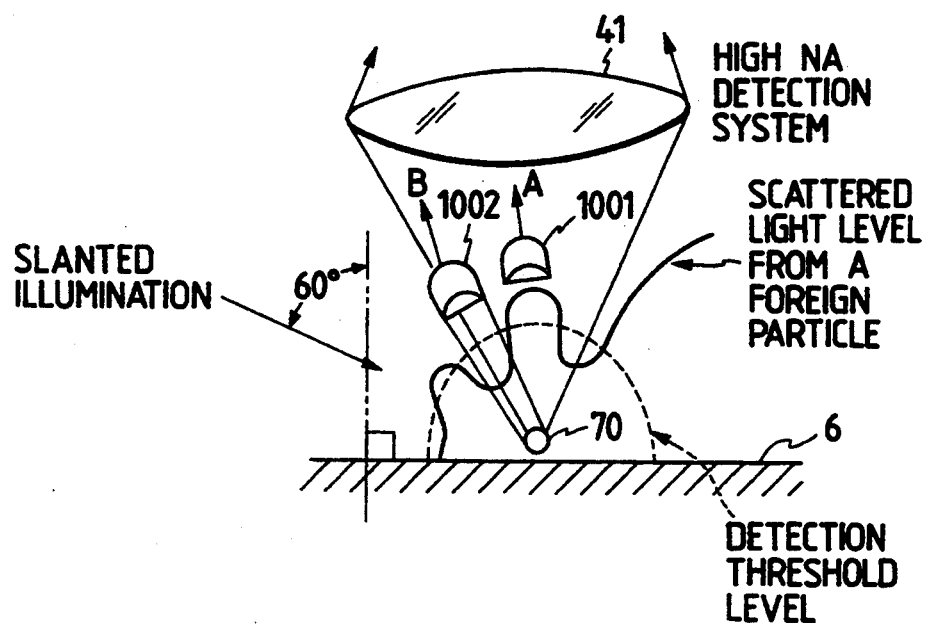
FIG. 13 is a drawing for explaining problems of the prior art.

FIG. 11 is a drawing for explaining an embodiment of foreign particles which are missed by the prior art, FIG. 12 is a drawing for explaining problems of the prior art, and FIG. 13 is a drawing for explaining problems of the prior art.

Figure 11A:
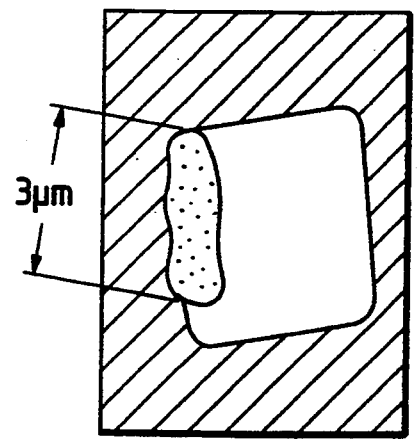
FIGS. 11(A)-(C) is a drawing for explaining an embodiment of foreign particles which are missed by the prior art.
Figure 11B:
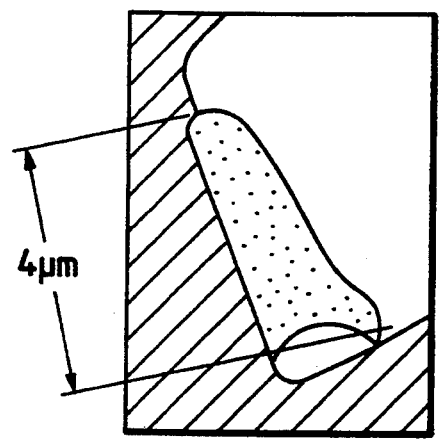
Figure 11C:
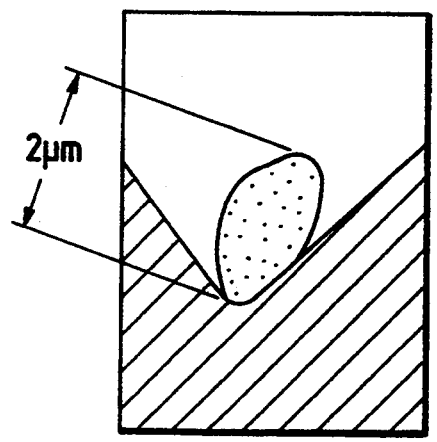

These foreign particles shown in FIGS. 11(A) to 11(C) are those which can be detected from a view point of size.

The present invention investigates the missing mechanism by the prior art and proposes a foreign particle inspection method using a new structure.

In a foreign particle inspection apparatus on a reticle shown in FIG. 12 wherein problems of the prior art are explained, a method that diffracted light from a circuit pattern formed on the reticle is eliminated and only scattered light from foreign particles is detected is an important point of the art.

For that purpose, methods for analyzing the polarization status of scattered light or comparing outputs of a plurality of detectors have been developed and put to practical use. To avoid effects of scattered light generated from a circuit pattern, an optical system with a small aperture such as a NA of about 0.1 is arranged slantwise so as to avoid scattered light from the circuit pattern. In this structure, a problem that irregularly shaped foreign particles may be easily missed is imposed by the reason which will be described later.

The aforementioned NA is a numerical value representing the characteristic of a lens which is determined by the aperture diameter of the lens and the distance up to the target object. Concretely, the NA is a numerical value which is obtained from $NA = \sin \theta$ using $\theta$ shown on the right of FIG. 12.

Another problem is a pattern elimination art for dealing with refined circuit patterns which is used in various inspection arts on an auxiliary basis. Most inspection arts use a method that when a circuit pattern is found during inspection, the detection sensitivity of a foreign particle detector is automatically lowered. In this method, a problem is imposed that foreign particles near the pattern edge are missed although the circuit pattern maldetection is reduced.

Countermeasures of the present invention for the above two problems will be described hereunder.

Figure 14:
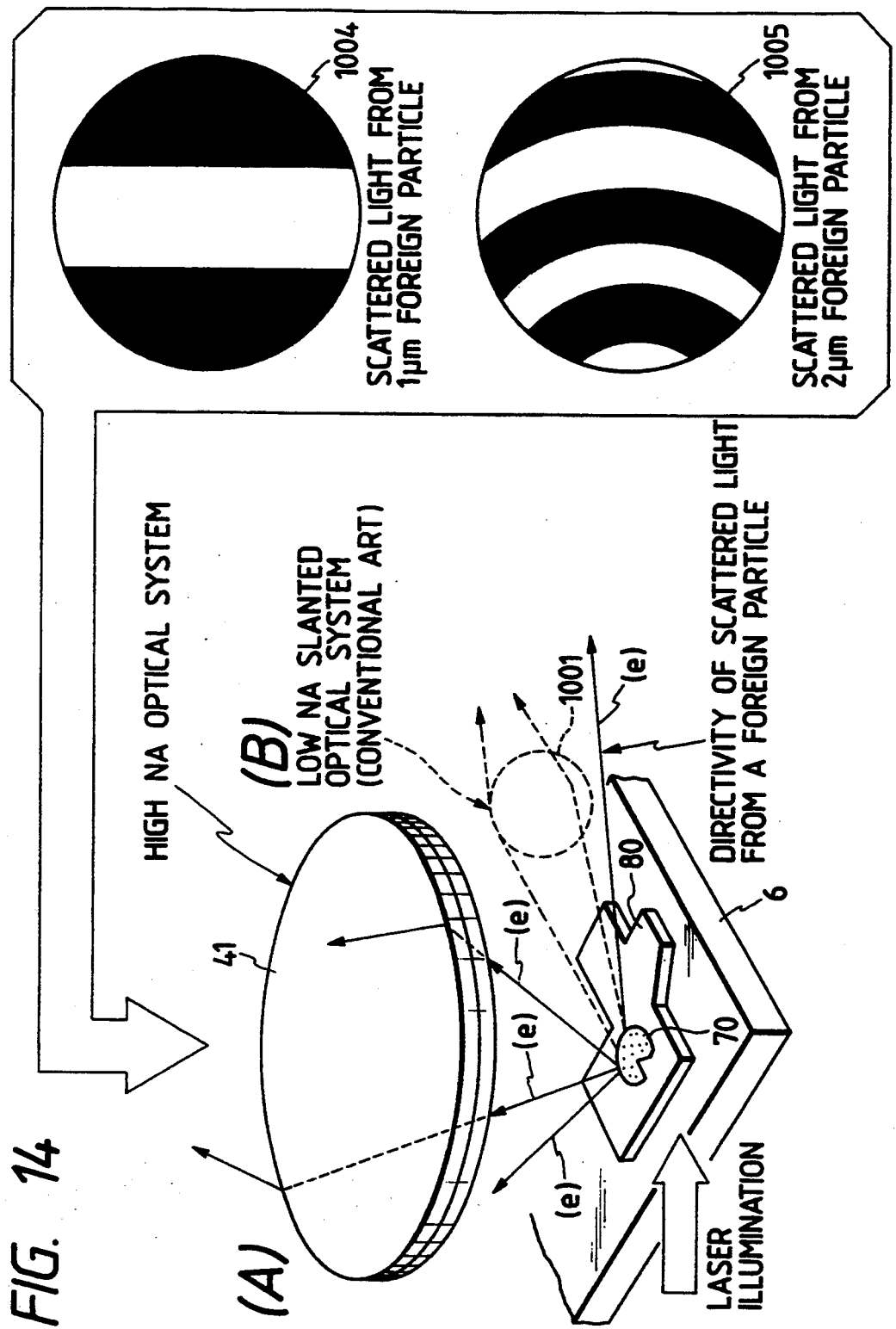
FIGS. 14(A)-(B) is a drawing for explaining detection of scattered light from foreign particles using a high NA optical system according to the present invention.
Figure 15:
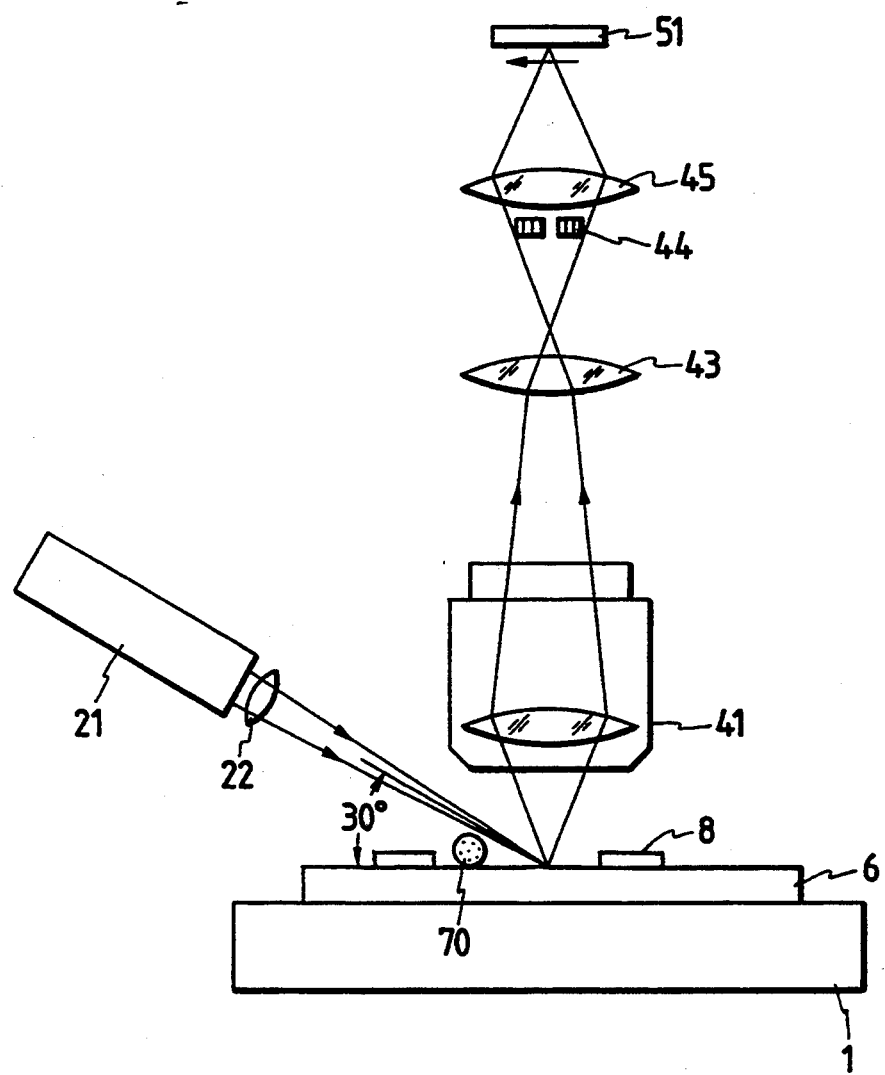
FIG. 15 is a structural diagram showing main parts of the equipment shown in FIG. 1.
Figure 17B:
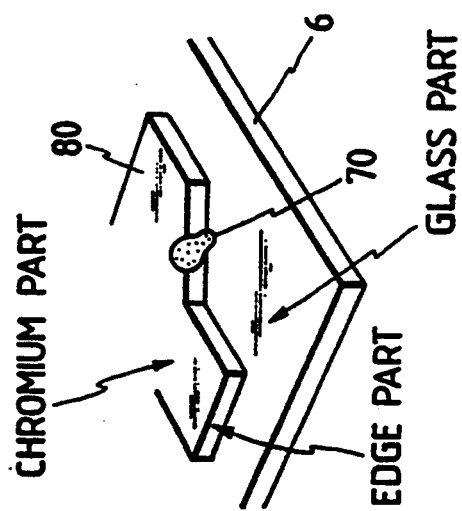
FIGS. 17A-B depict a columnar graph and a corresponding illustration showing the result of classification of the detected foreign particles shown in FIG. 16 by foreign particle adhered location.
Figure 17A:
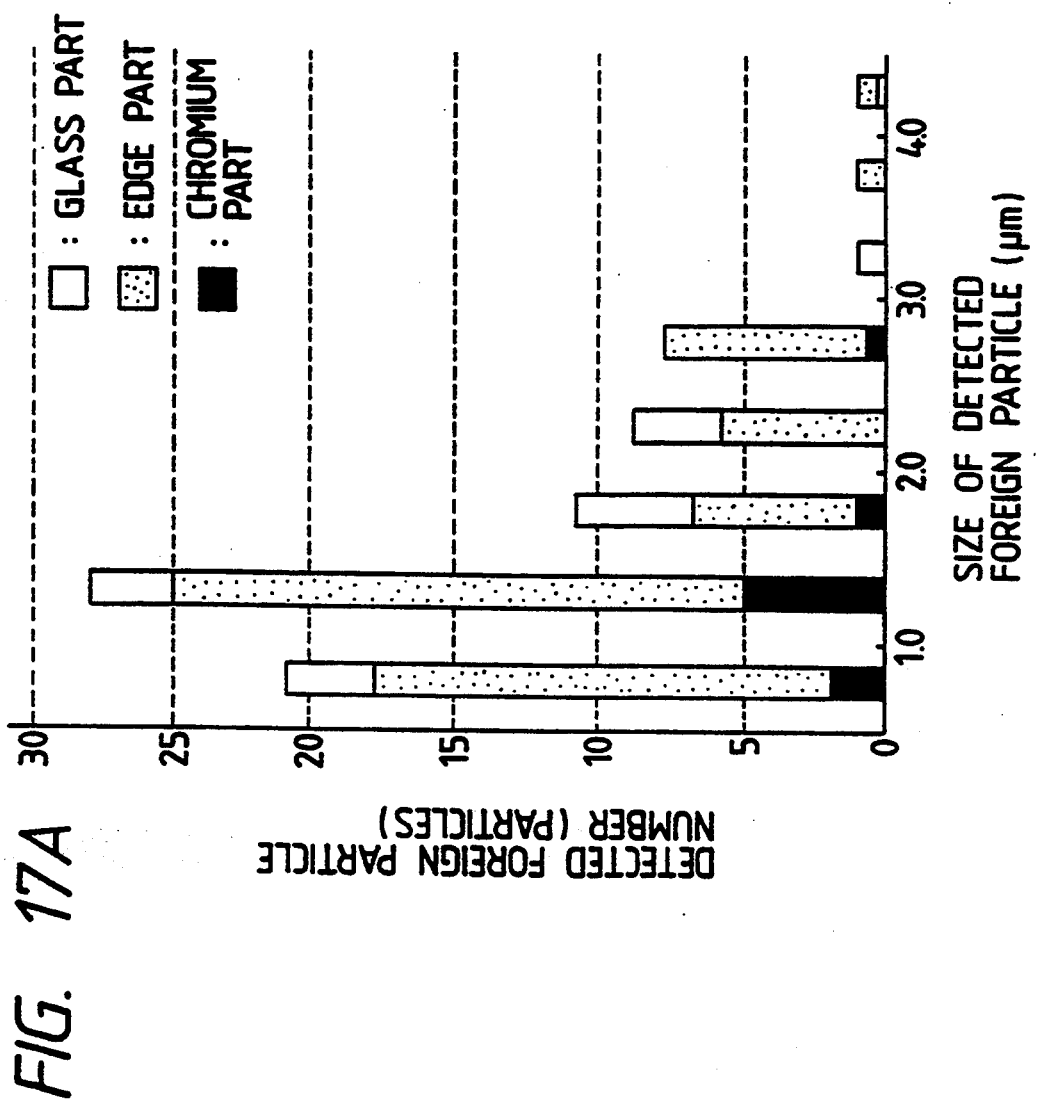

FIGS. 14A–B are drawings for explaining detection of scattered light from foreign particles using a high NA optical system according to the present invention, FIG. 15 is a structural diagram showing main parts of the equipment shown in FIG. 1, FIG. 16 is a columnar graph showing the number of detected foreign particles vs the size of detected foreign particles by the present invention and the prior art, and FIGS. 17A–B depict a columnar graph and corresponding illustration showing the result of classification of the detected foreign particles shown in FIG. 16 by foreign particle adhered location.

Images 1004 and 1005 shown in FIGS. 14A–B are scattered lights generated when a laser beam is irradiated to foreign particles, which are observed from the top. A point of these images which attracts a great deal of attention is that scattered light (e) from the foreign particles is distributed directionally. Therefore, in the case of a conventional low NA detector 1001 indicated by a dashed line, when the detector is not adequately located, the scattered light (e) generated from a foreign particle does not always enter into the low NA optical system satisfactorily, causing missing. Furthermore, the distribution status of these scattered lights varies with the foreign particle size and shape, and it is practically impossible to arrange the low NA optical system adequately for all foreign particles.

The result when this is experimentally measured is shown in FIG. 13.

In the scattered light distribution when a foreign particle is illuminated by a laser beam at an incident angle of 60°, the scattered light level from the above foreign particle is measured by changing the detection angles of the low NA ($NA \approx 0.1$) detection optical systems 1001 and 1002. This drawing shows that although the detection level at point A1001 is more than the detection threshold level, the detection level at point B1002 is not more than the detection threshold level and hence the foreign particle cannot be detected. This indicates that since the scattered light distribution of an actual foreign particle is not fixed, the low NA detection method such as A and B does not provide shable detecting precision.

Therefore, the present invention provides a method that scattered lights from foreign particles having various scattering distributions are effectively condensed by a high NA detection optical system 41 having a large aperture.

The effect of the present invention when a foreign particle 70 on a reticle 6 is detected by an apparatus comprising a laser 21, a condensing lens 22, an object lens 41, a field lens 43, a spatial filter 44, an imaging lens 45, and a detector 51 as shown in FIG. 15 is shown in FIG. 16.

In FIG. 16, the total number of foreign particles detected on five reticles is given in the vertical axis and the size of detected foreign particles is given in the horizontal axis. The total number and size of foreign particles which are detected also by the prior art are shown in a different color.

It is said that the detection capability of the prior art is 0.8 μm. Therefore, it is understandable that the detection capability of the prior art in an area of foreign particles less than 1 μm in size is lower than that of the present invention. Even in an area of foreign particles more than 1 μm in size, the number of detected foreign particles of the present invention is extremely large. The detection ratio of the present invention to the prior art is about 10 times.

This is possibly because the high NA detection optical system used by the present invention detects scattered light from irregularly shaped foreign particles stably.

Next, the detection status of foreign particles adhered at the circuit pattern edge will be explained. The result when the detected foreign particles shown in FIG. 16 are classified by foreign particle adhered position is shown in FIGS. 17A–B. The adhesion positions on the reticle circuit pattern side are classified into three areas such as the glass part (transmission part), chromium part (shielding part which is often formed by a metallic film such as chromium), and the edge part which is a boundary part of the two. Among them, the edge part is greatly affected by adhered foreign particles and foreign particles adhered on the chromium part will not affect transfer so long as they remain on the chromium part.

It is clearly shown in FIGS. 17A–B that the detecting precision for foreign particles on the edge part which affect transfer most, that is, are required to be detected most is improved.

Figure 18:
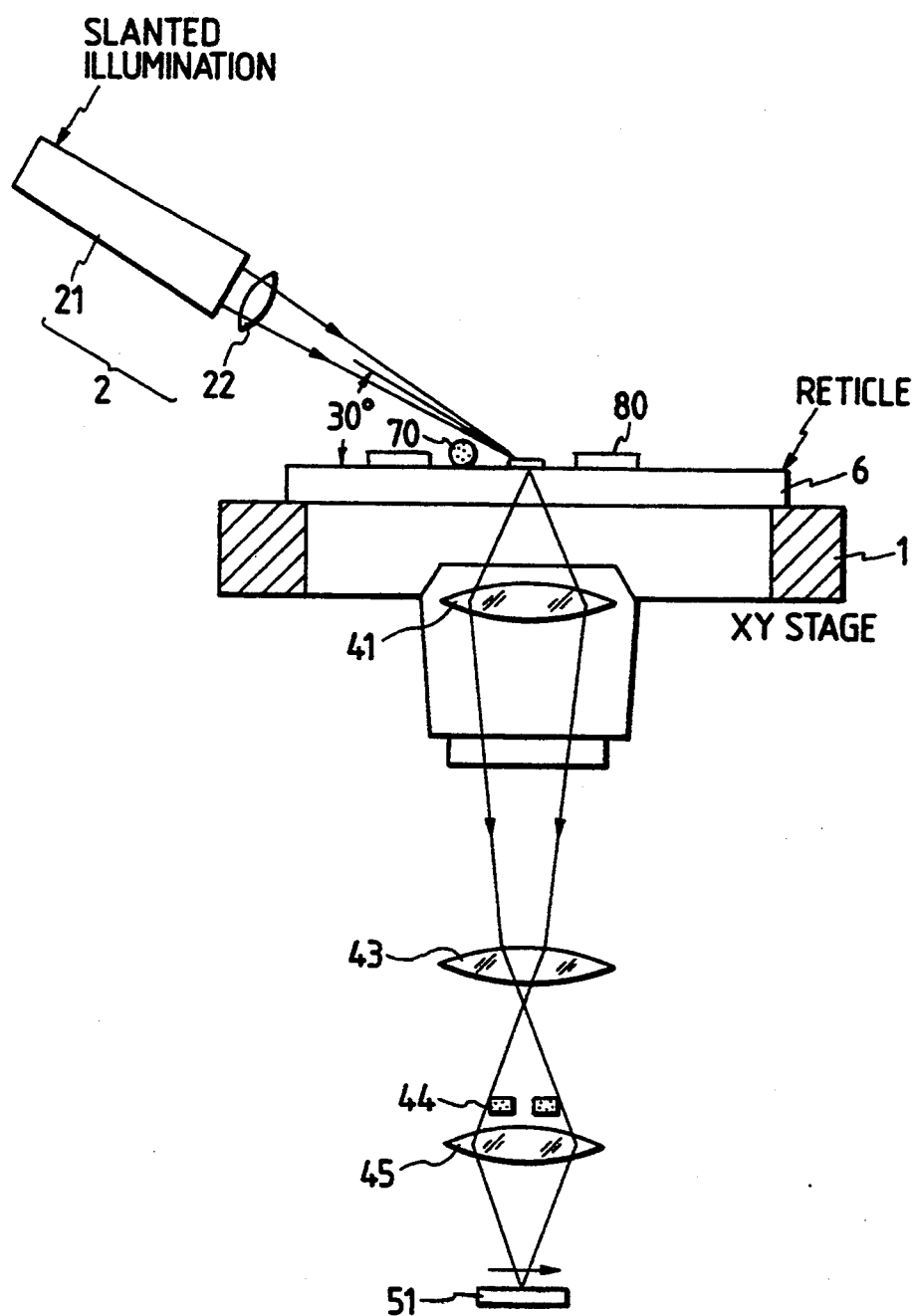
FIG. 18 is a structural diagram of the essential section of a foreign particle inspection apparatus according to another embodiment of the present invention.

When the aforementioned idea that foreign particles on the chromium part are not brought into question is used, the structure show in FIG. 18 is also available.

FIG. 18 is a structural diagram of the essential section of a foreign particle inspection apparatus according to another embodiment of the present invention.

In the example shown in FIG. 18, the layout of the illumination system comprising the laser 21 and the condensing lens 22 is the same as with the example shown in FIG. 15, though the detection optical system comprising the object lens 41, the field lens 43, the spatial filter 44, and the imaging lens 45 and the detector 51 are arranged on the rear side of the surface of the reticle 6 whereon a circuit pattern 80 is formed.

In this case, although foreign particles on the chromium part cannot be detected, scattered lights from foreign particles on the glass and edge parts, which adversely affect transfer, can be detected via the reticle 6 which is a transparent substrate.

Figure 19:
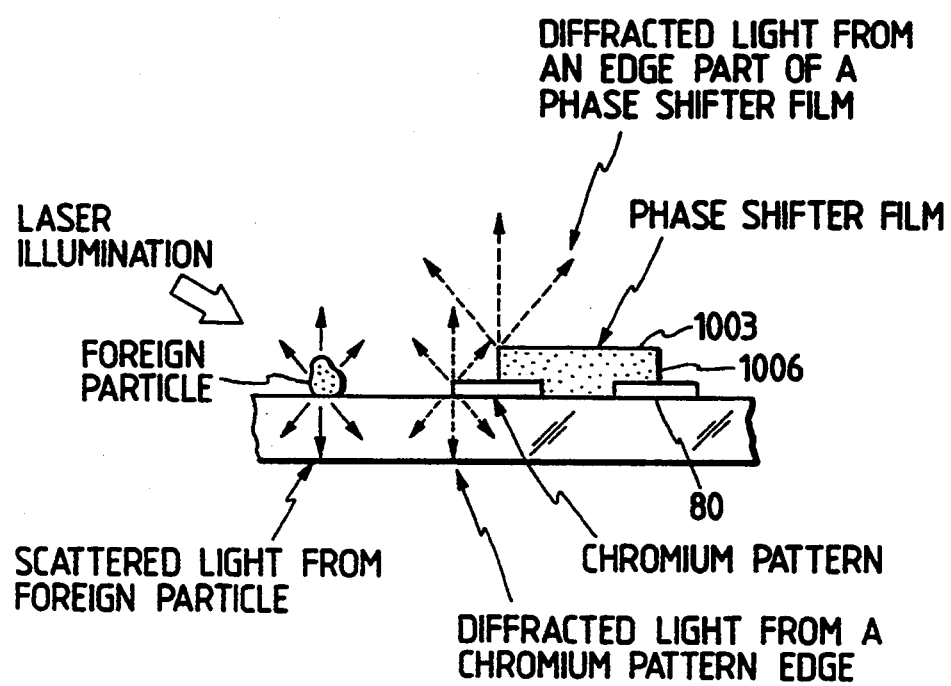
FIG. 19 is a drawing for explaining scattered light and diffracted light from a reticle with a phase shifter film according to the present invention.

An advantage of this structure is that a reticle with the section shown in FIG. 19 can be processed.

Figure 20:
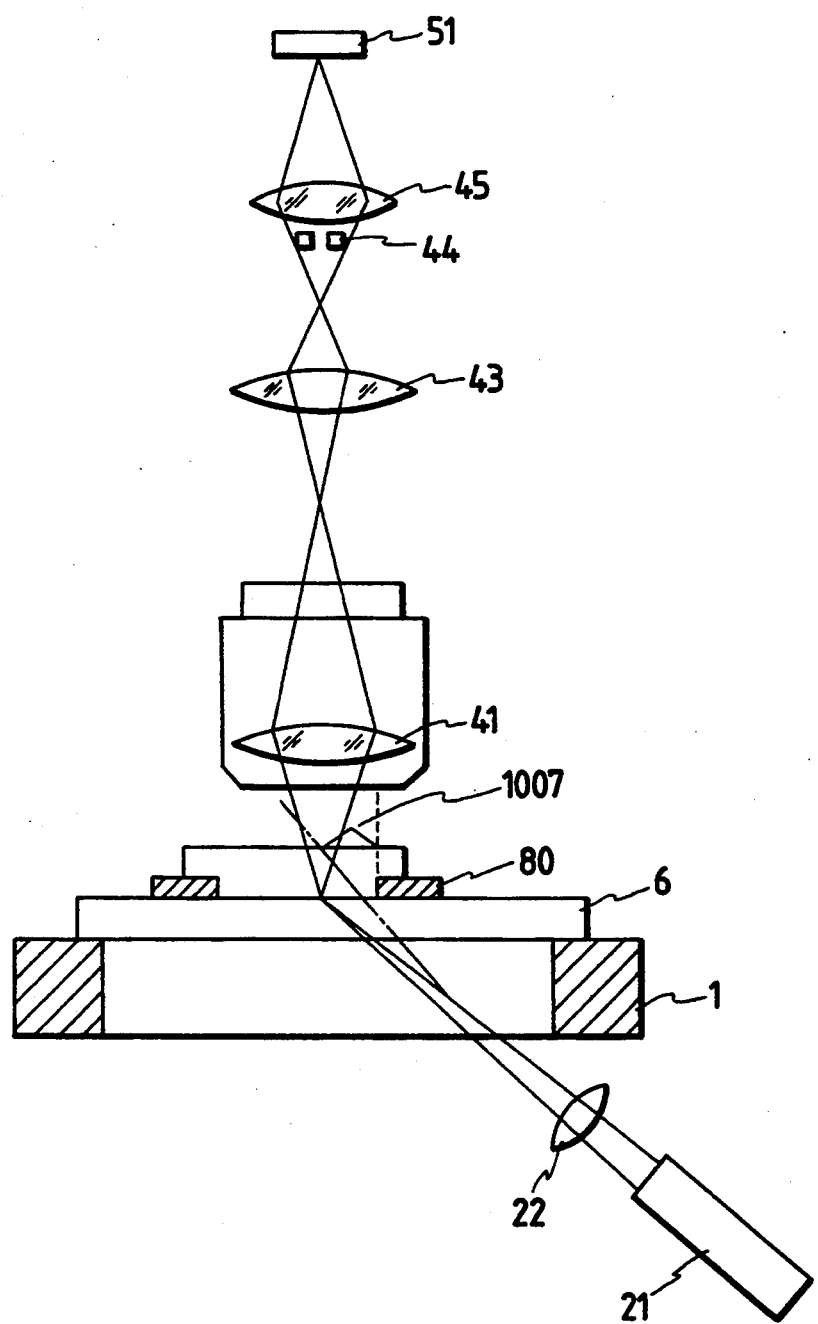
FIG. 20 is a structural diagram of the essential section of a foreign particle inspection apparatus according to a further embodiment of the present invention.
Figure 21:
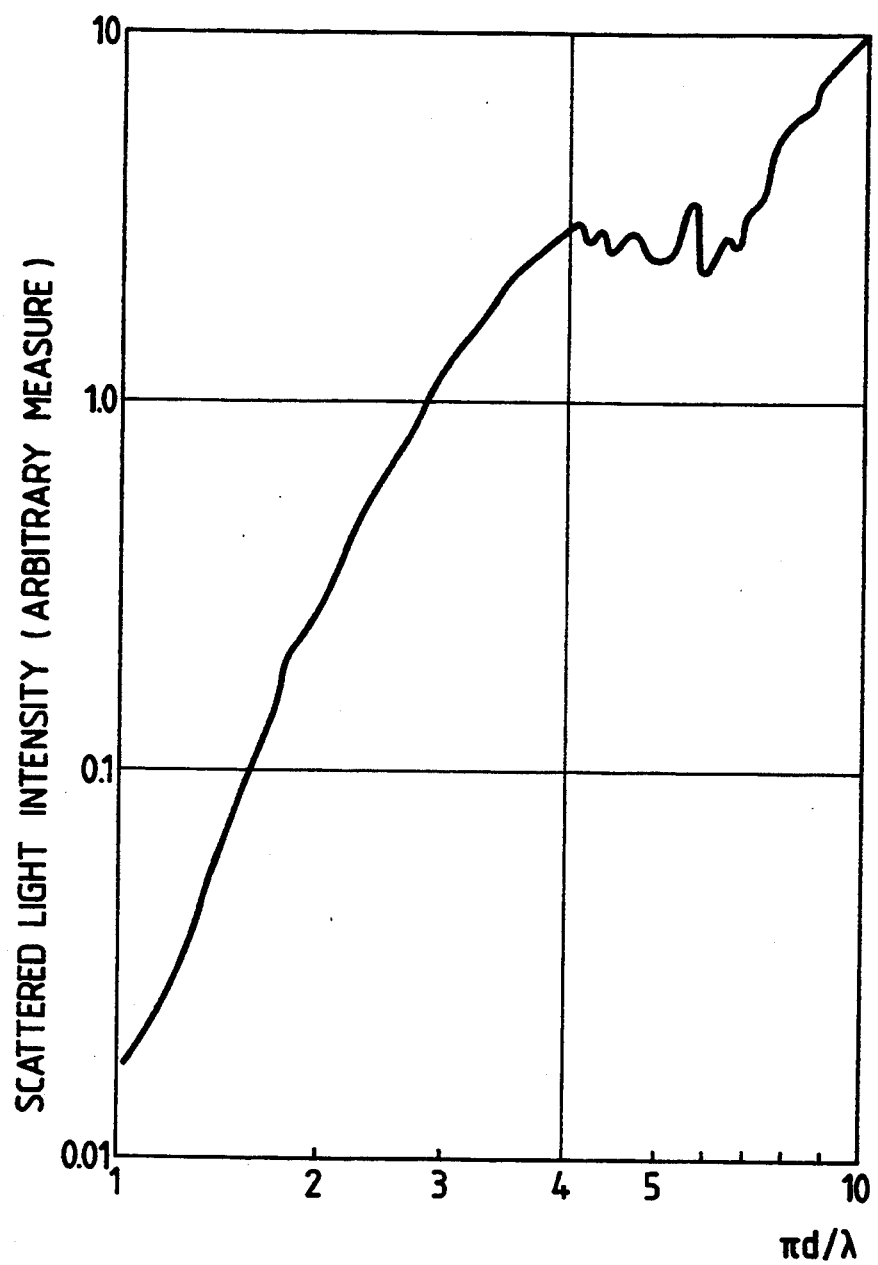
FIG. 21 is a drawing showing the theoretical value of scattered light intensity from foreign particles vs a dimensionless number of $\pi D/\lambda$ using a wave length of $\lambda$ of a laser beam and a foreign particle diameter of D.
Figure 22:
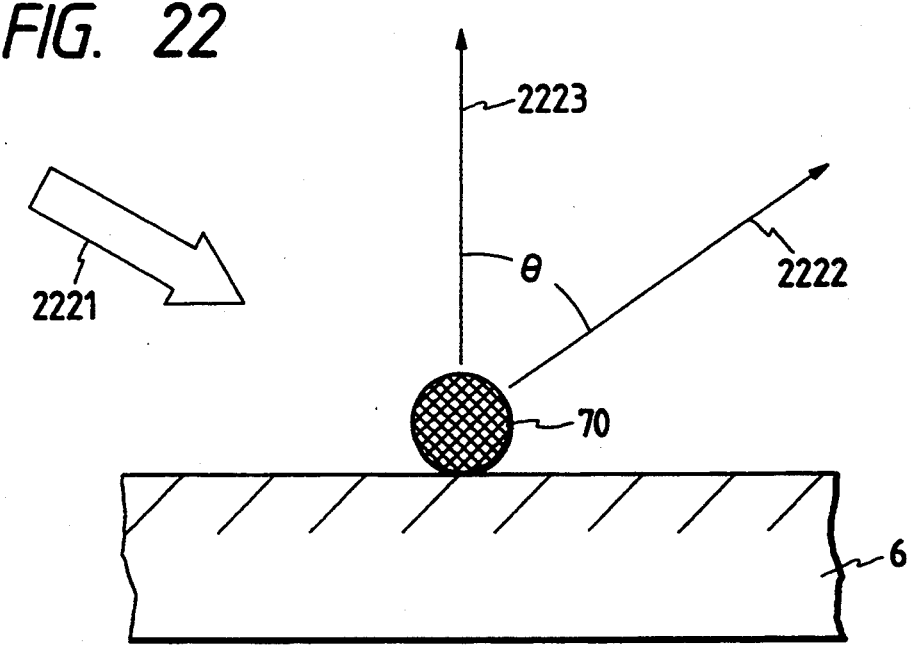
FIG. 22 is a drawing for explaining the direction of diffracted light from a foreign particle.
Figure 23:
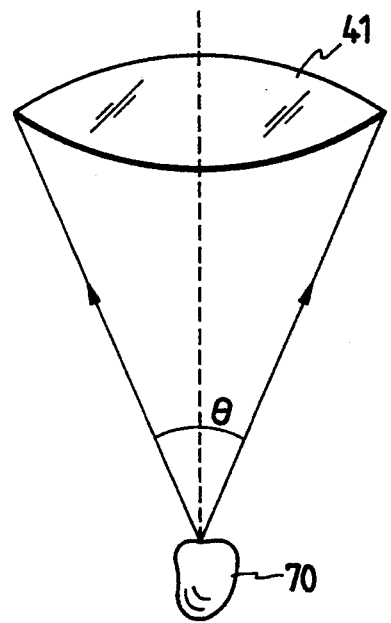
FIG. 23 is a drawing for explaining the definition of NA of an optical system.
Figure 24:
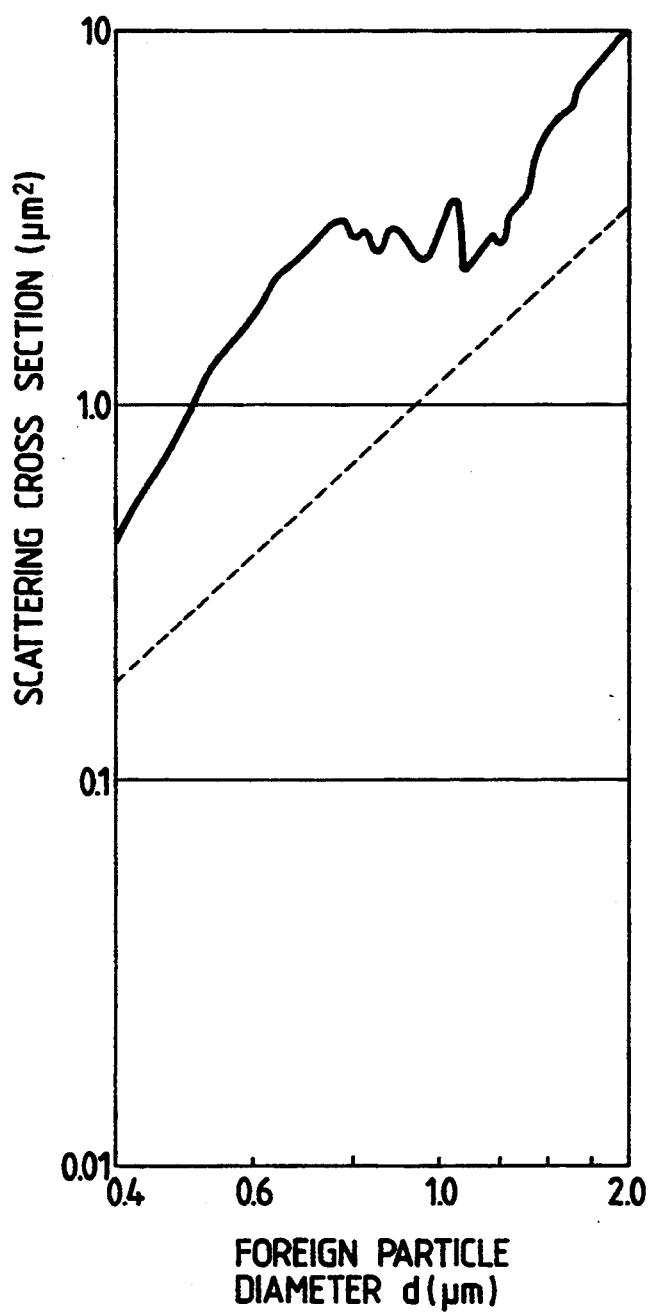
FIG. 24 is a chart showing the scattering cross section, which is proportional to the scattered light intensity from foreign particles, vs the foreign particle diameter.

FIG. 19 is a drawing for explaining scattered light and diffracted light from a reticle with a phase shifter film according to the present invention and FIG. 20 is a structural diagram of the essential section of a foreign particle inspection apparatus according to a further embodiment of the present invention.

On the reticle shown in FIG. 19, a pattern (shifter pattern) 1003 of a phase shifter film for improving the patterning resolution is installed between the chromium parts. This film is transparent but has a structure that the size is several times of that of the chromium part (the thickness is about 0.1 $\mu m$). Therefore, diffracted light from the edge part 1006 thereof is larger than diffracted light from the edge part of the chromium part.

However, in a structure that the detection optical system is installed at the lower part as shown in FIG. 18, diffracted light generated from the shifter pattern 1003 is shielded by the chromium part of the reticle itself and does not enter into the detection optical system, producing no effect on detection of foreign particles.

In this example, the reticle, the illumination system 2, and the object lens 41 are arranged as shown in the drawing. However, the object of the present invention can be accomplished by shielding scattered light from the edge part 1006 of the phase shifter film pattern 1003 arranged on the chromium part by using the chromium part. Therefore, it is desirable that the illumination system 2 and the object lens 41 are installed on the opposite sides of the reticle 6 each other and the structure shown in FIG. 20 is also available.

However, since the shifter pattern 1003 has a thickness, a part 1007 which cannot be illuminated occurs in the case of slant illumination when the structure shown in FIG. 20 is used. Therefore, the structure shown in FIG. 18 is more desirable than that shown in FIG. 20.

Figure 34:
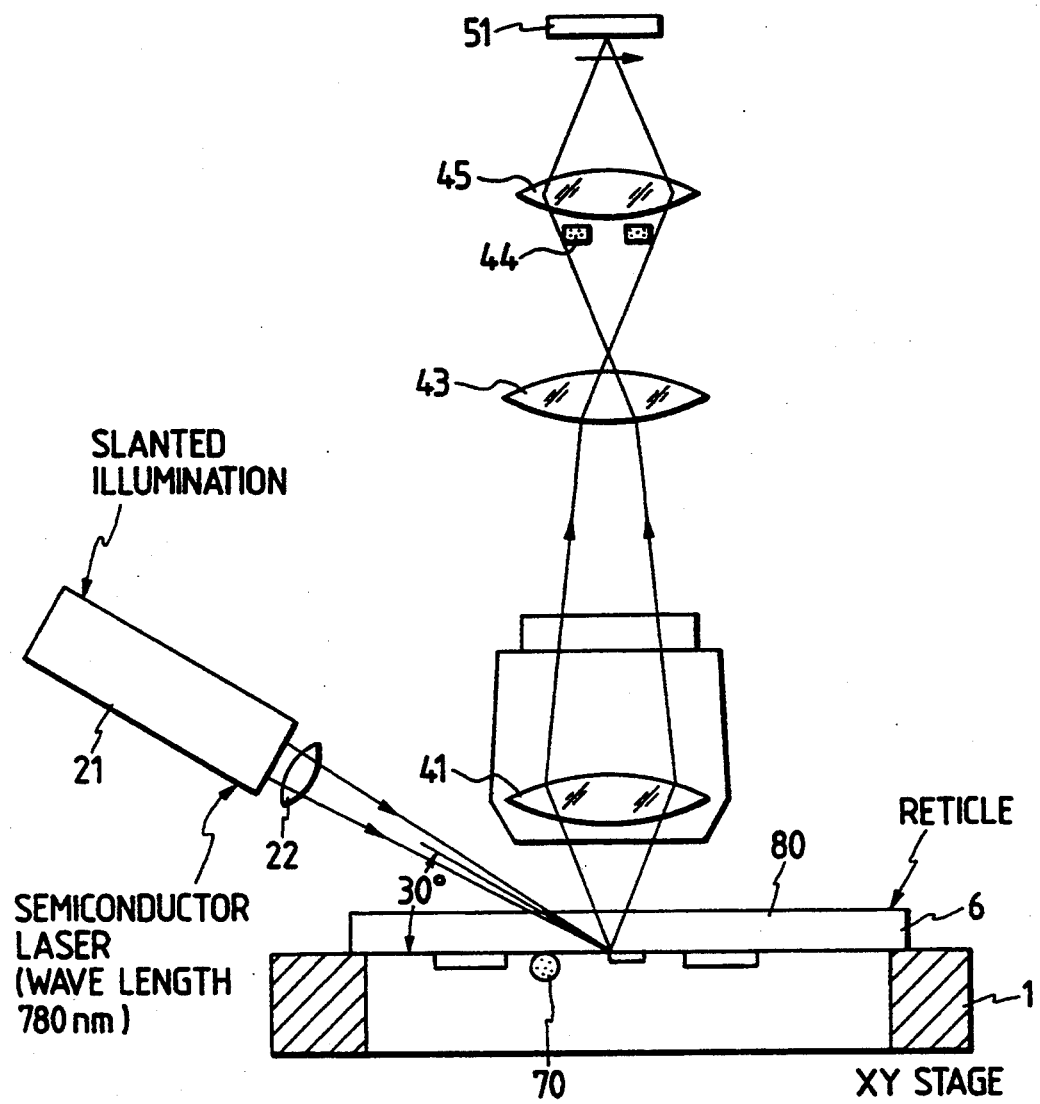
FIG. 34 is a structural diagram of the essential section of a foreign particle inspection apparatus according to a further embodiment of the present invention.

The structure shown in FIG. 34 that the illumination system and optical detector system are arranged on the rear side of the circuit pattern plane obtains the same good result.

FIG. 34 is a structural diagram of the essential section of a foreign particle inspection apparatus according to a further embodiment of the present invention.

It is mentioned above that the chromium part is not included in the inspection objects. However, when scattered lights from the front side and the rear side are detected by two optical detector systems using the structure shown in FIG. 1, the entire surface including the chromium part can be inspected with certain precision.

Figure 35:
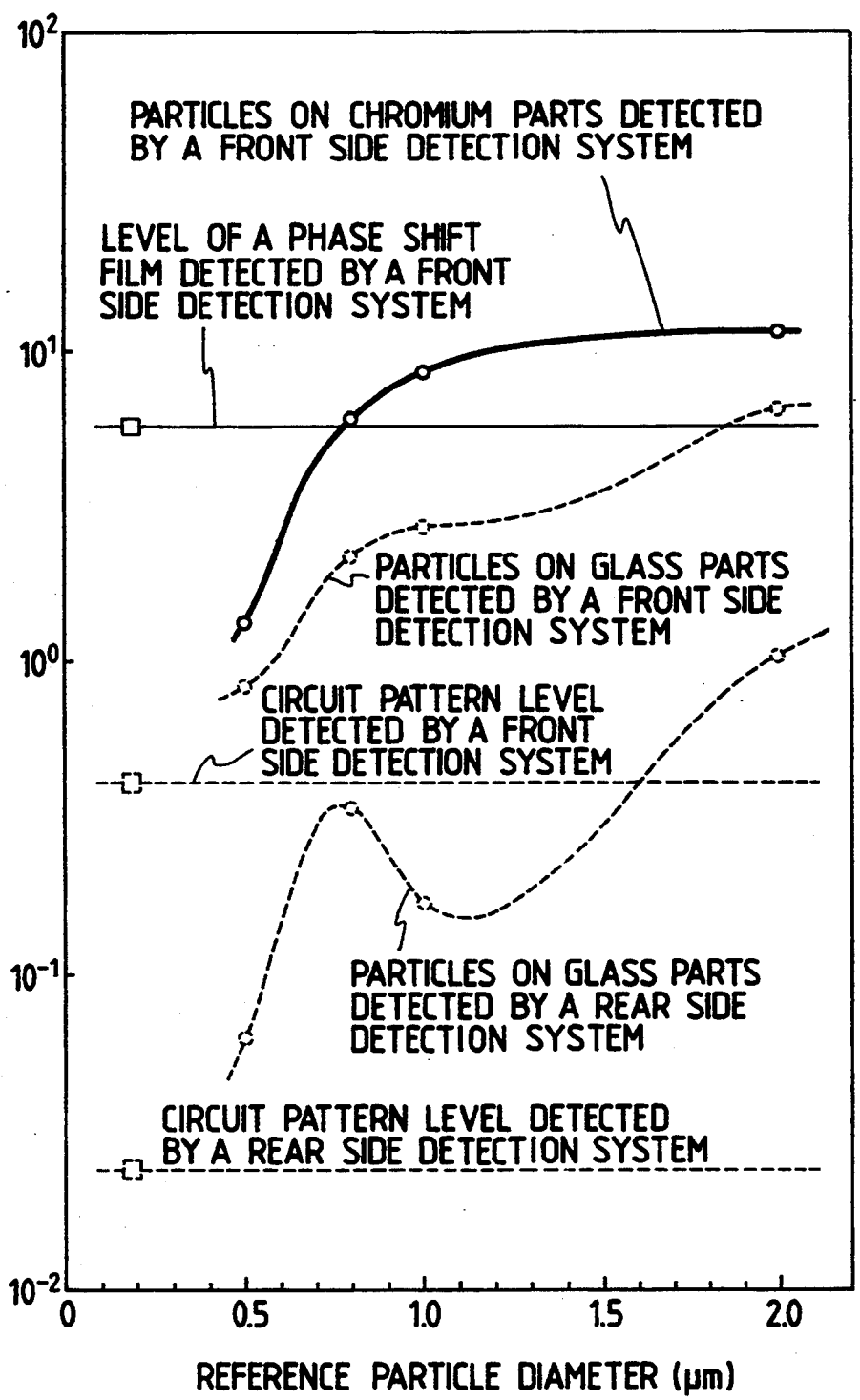
FIG. 35 is a chart showing output of a detector which detects scattered light from reference particles and circuit pattern corners according to the present invention.

FIG. 35 is a chart showing output of a detector which detects scattered light from reference particles and circuit pattern corners according to the present invention.

FIG. 35 shows scattered light detected outputs from the reference particles which are model foreign particles of a front side detector system (numeral 4 shown in FIG. 1) and a rear side detector system (numeral 40 shown in FIG. 1), the circuit pattern (edge part of the chromium part), and the shifter pattern.

In FIG. 35, the horizontal axis represents the particle diameter and the vertical axis represents scattered light detected output. Particles which have outputs more than the scattered light detected output levels from the circuit pattern and phase shifter film which are shown by horizontal lines in the drawing can be detected. The drawing shows that the scattered light from the reference particles on the chromium parts has an output level which is several times of the output level of the reference particles on the glass parts, and particularly when the particle size is more than 0.8 microns, the output level from the scattered light on the chromium parts is higher than the level of the scattered light from the phase shifter film.

Although foreign particles on the chromium parts are affected by the phase shifter, foreign particles more than 0.8 microns in size can be detected. Therefore, the present invention provides a structure that foreign particles on the glass parts are detected by the rear side detector system and foreign particles on the chromium parts are detected by the front side detector system as shown in FIG. 1 and also foreign particles which may move from the chromium parts to another position can be detected.

Also in the following case, it is necessary to detect foreign particles on the chromium parts.

The aforementioned concept that foreign particles on the chromium parts are allowed is realized principally at the time of exposure. However, in the manufacture process for reticles with a phase shift film, foreign particles on the chromium parts may be brought into question.

A reticle with a phase shift film is generally manufactured by a method that a film is formed on the entire surface of a substrate by coating or sputtering a shifter film material after the chromium parts are formed (the processing up to this process is the same as that for a reticle without a phase shift film) and a pattern (shift pattern) is formed by the shifter film using the etching process. When foreign particles exist on the chromium parts before film forming, the film forming is adversely affected and defects such as air bubbles or chips may occur in the shifter film. Therefore, in addition to the aforementioned foreign particle inspection after shifter pattern forming, it is necessary to inspect foreign particles (by the method of the present invention, defects such as air bubbles and chips can be detected in the same way as foreign particles) on the entire surface including the chromium parts before and after film forming.

In this case, the shifter pattern is not formed yet and hence no scattered light is generated from the shifter pattern. Therefore, when a front side detector system is provided as shown in FIG. 1, the entire surface can be detected on a highly sensitive basis.

Particularly when foreign particles are detected and decided pixel by pixel by an array detector, the following faults occur.

Figure 25:
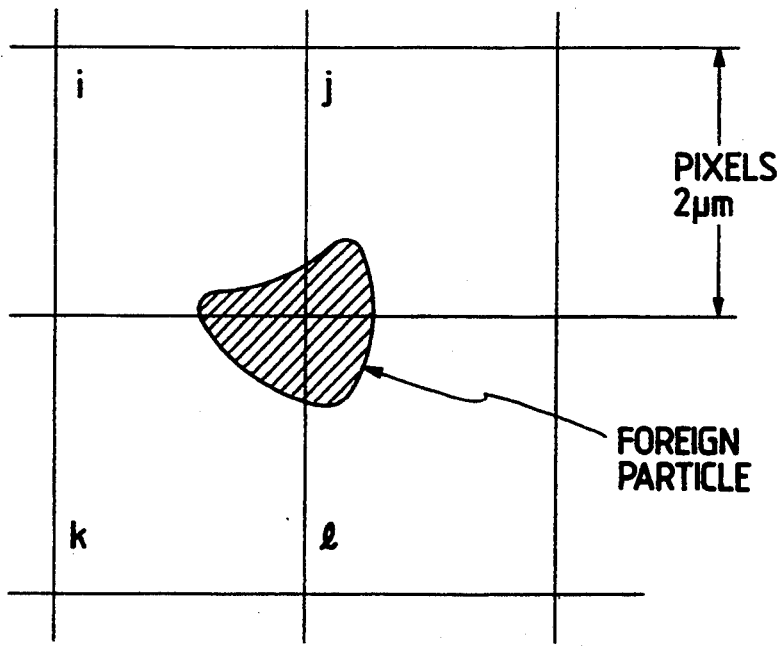
FIG. 25 is a drawing for explaining detection of foreign particles by 2 by 2 μm² pixels without performing 4-pixel addition.
Figure 26:
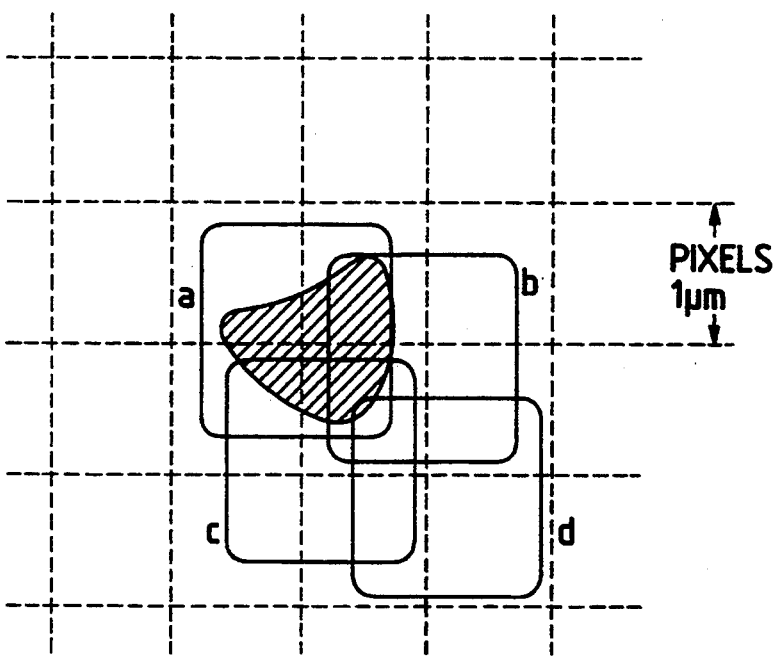
FIG. 26 is a drawing for explaining detection of foreign particles by 1 by 1 μm² pixels by performing 4-pixel addition.
Figure 27:
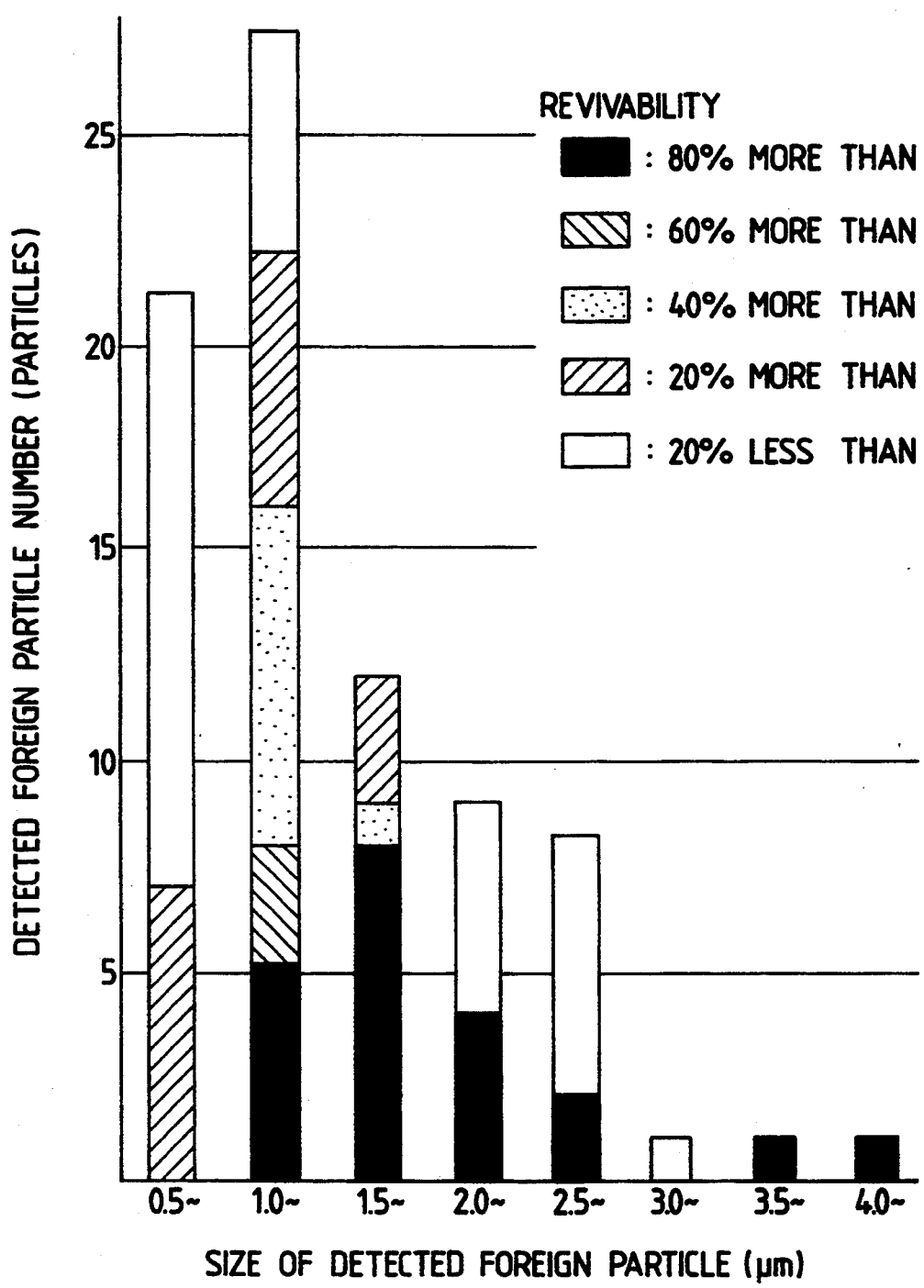
FIG. 27 is a columnar graph showing an example of the foreign particle revivability of the present invention when the 4-pixel addition is not applied.
Figure 28:
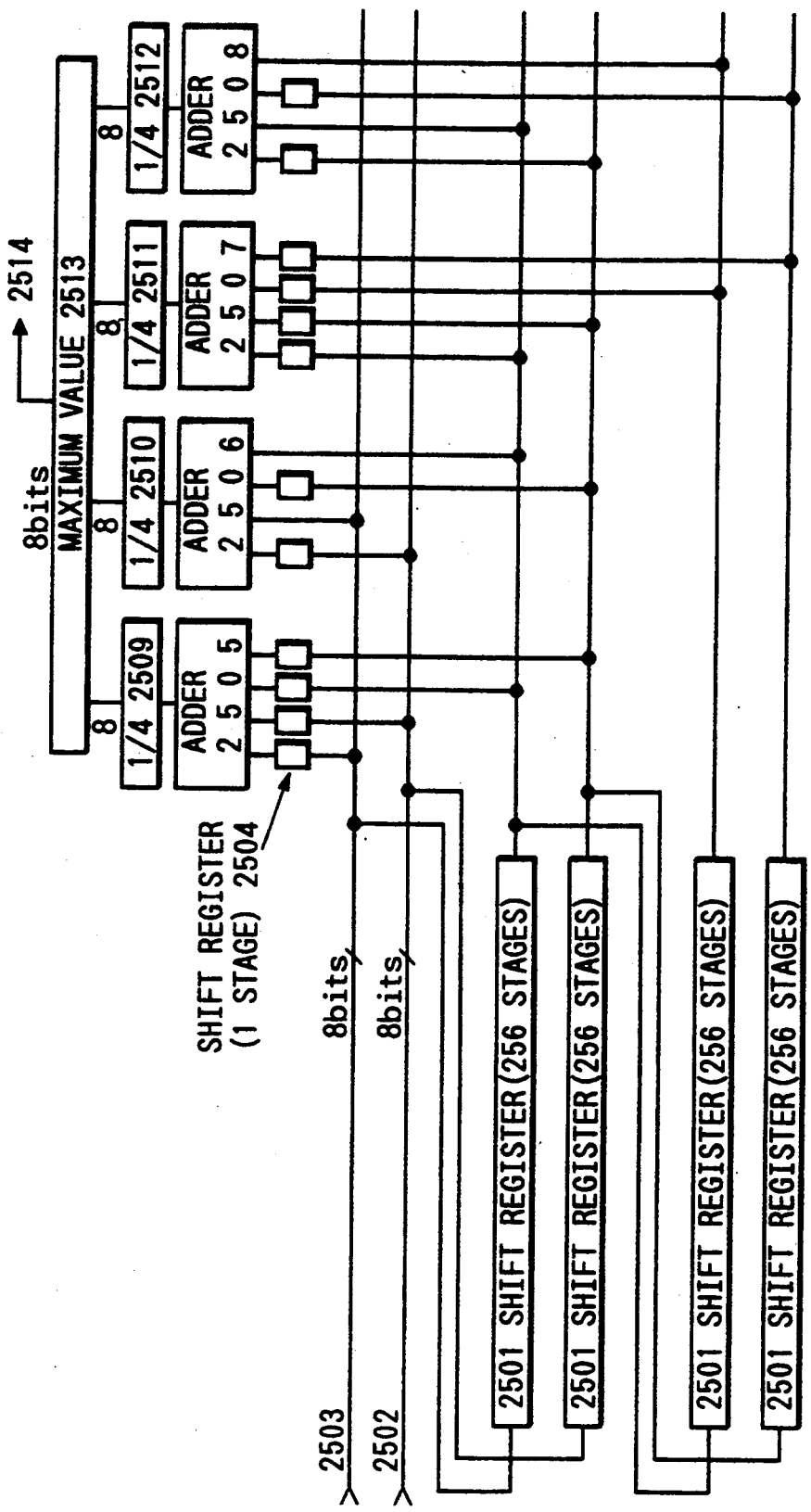
FIG. 28 is a block diagram of an example of a 4-pixel addition circuit.

FIG. 25 is a drawing for explaining detection of foreign particles by 2 by 2 $\mu m^2$ pixels without performing 4-pixel addition, FIG. 26 is a drawing for explaining detection of foreign particles by 1 by 1 μm² pixels by performing 4-pixel addition, FIG. 27 is a columnar graph showing an example of the foreign particle revivability of the present invention when the 4-pixel addition is not applied, and FIG. 28 is a block diagram of an example of a 4-pixel addition circuit.

In an example that the pixel size of a detector 2 by 2 μm² is used for detection and decision of foreign particles, as shown in FIG. 25, under the condition that a foreign particle is detected over a plurality (from 2 to 4) of pixels, scattered light from the foreign particle is also dispersed to a plurality of pixels and as a result, the detected output of one pixel is reduced to ½ to ¼ (actually about ⅓ by the effect of crosstalk between the detector and the pixel) and the foreign particle detection rate decreases.

The location relationship between detector pixels and small foreign particles is very fine due to the size and changed for each inspection. In this case, the result varies with inspection even for the same sample and the revivability lowers.

Therefore, as shown in FIG. 26, the detection pixel size is reduced to 1 by 1 μm², and the detected outputs of four 1 by 1 μm² pixels neighboring each pixel are electrically added, and the detected output by a 2 by 2 μm² pixel is simulated. The detected output is obtained duplicatedly in units of 1 μm (a, b, c, and d in the drawing) and the maximum value (a in the drawing) is used for detection and decision of foreign particles as a representative output by a 2 by 2 μm² pixel. By doing this, the variation in the detected output from the same foreign particle is actually reduced to ±10% and the revivability of more than 80% can be ensured for all foreign particles.

FIG. 16 shows the result when a 4-pixel addition circuit is applied (the revivability is more than 80%).

An example of revivability before application is shown in FIG. 27. The drawing shows that the revivability cannot be ensured sufficiently unless the 4-pixel addition is performed.

FIG. 28 shows a block diagram of a concrete example of the 4-pixel addition circuit. The block diagram shows a one dimensional imaging device wherein 512 pixels which are reduced to 1 μm each are arranged. It is an example of a (general) one-dimensional imaging device wherein an output 2503 from the pixels of odd numbers of the one-dimensional imaging device and an output 2502 from the pixels of even numbers are outputted independently. Four pixels (2 by 2 pixel) which are shifted in the four directions in units of 1 pixel (1 μm) which is reduced by a 256-stage shift register 2501, a 1-stage shift register 2504, and adders 2505 to 2508 are added and a mean value of the mean values is obtained by dividers 2509 to 2512. The maximum value of the values in the four directions is obtained by a maximum value decision circuit 2513 and outputted as a detected value 2514 from foreign particles.

This method illuminates only foreign particles by optical processing for detection. Therefore, when a signal detected by the set threshold value is large, it is decided (binarized) that there is a foreign particle and the foreign particle can be detected. However, in the detected signal, (1) there are variations (about ±15%) in the sensitivity characteristics of each pixel of the one-dimensional imaging device detector and (2) there are sensitivity variations (shading) caused by the illumination distribution of the illumination light source.

Figure 29:
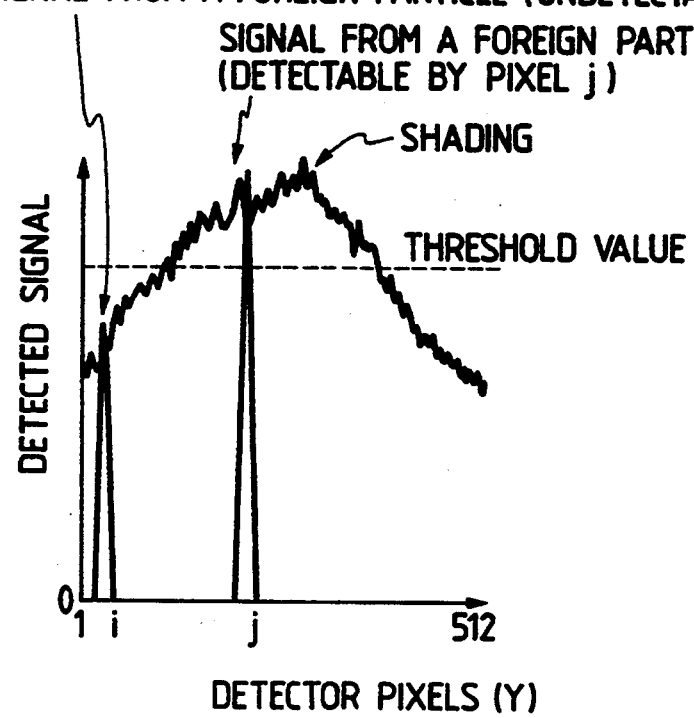
FIG. 29 is a chart showing an effect of shading on foreign particle detection.
Figure 30A:
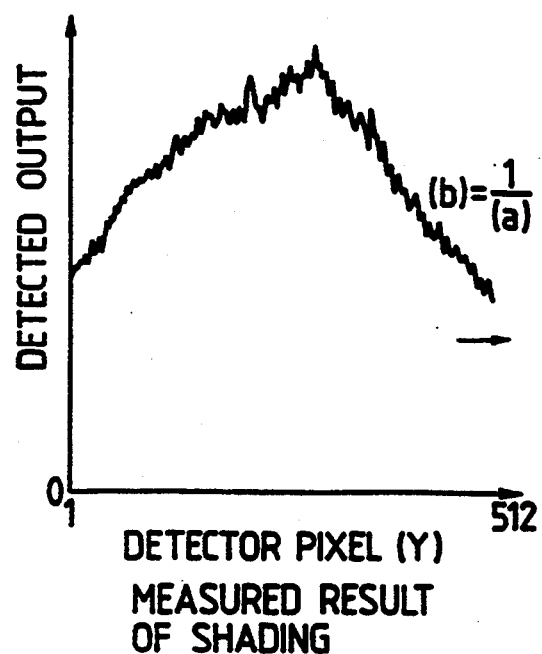
FIGS. 30(a)-(c) are drawings showing the shading principle.
Figure 30B:
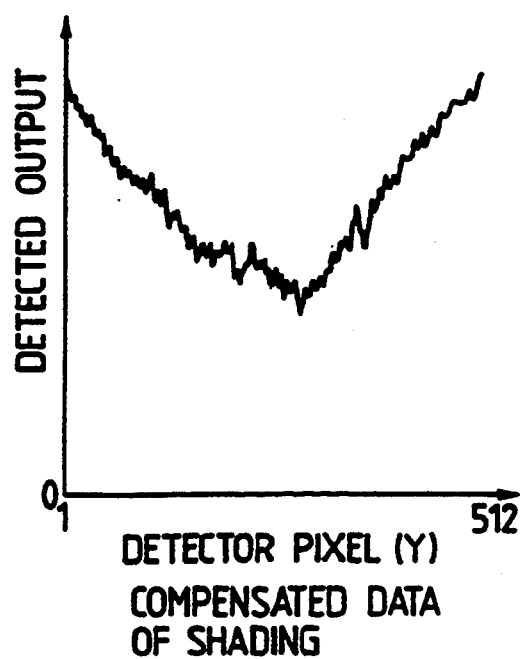
Figure 30C:
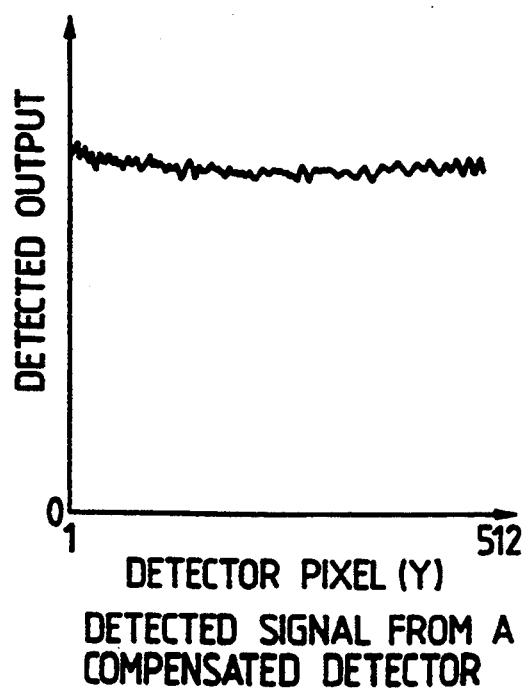
Figure 31:
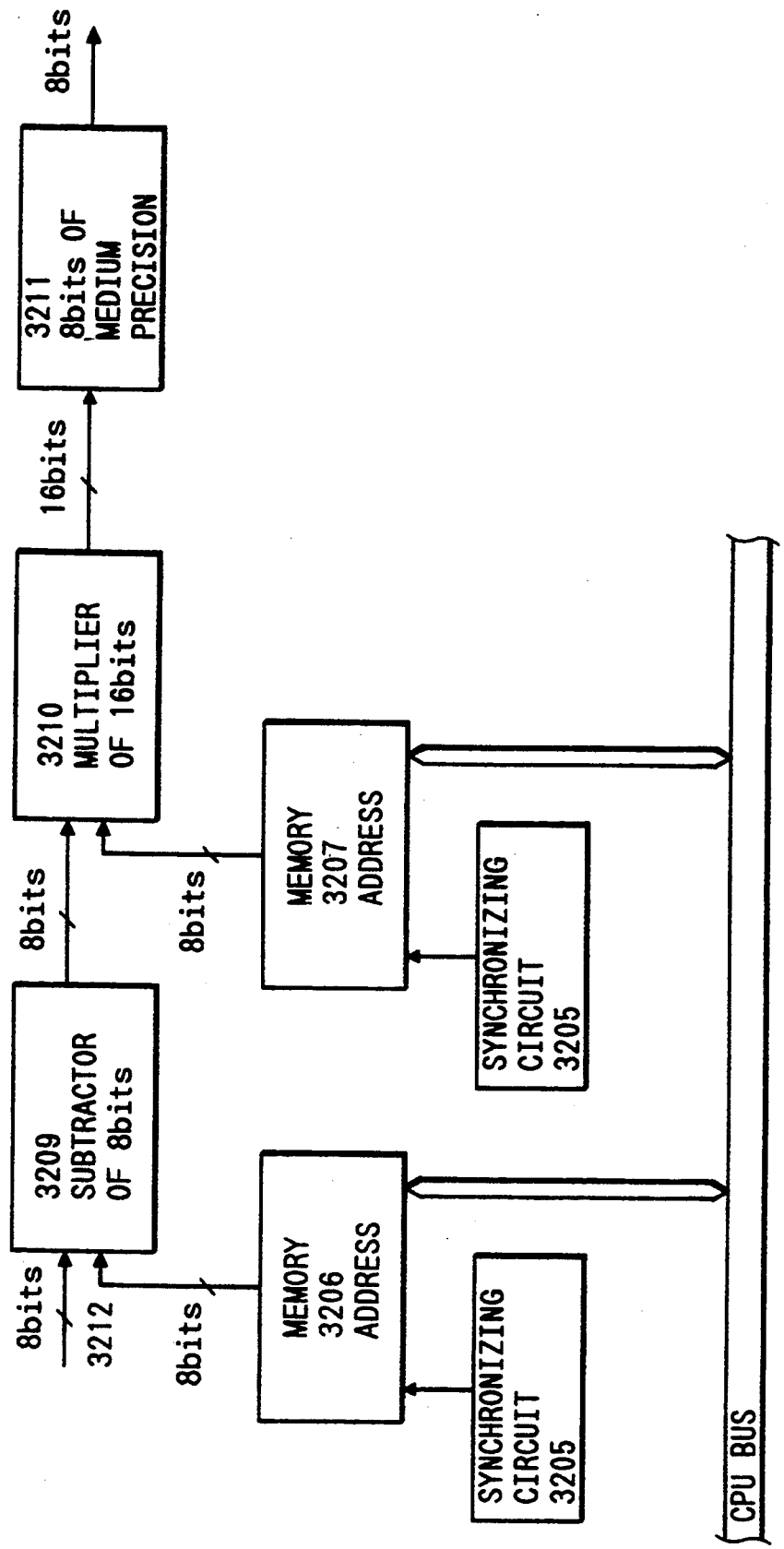
FIG. 31 is a block diagram of an example of a shading correction circuit.

FIG. 29 is a chart showing an effect of shading on foreign particle detection, FIGS. 30A–C are drawings showing the shading principle, and FIG. 31 is a block diagram of an example of a shading correction circuit.

The size of the detected signal varies with the detected pixel (the position in the Y direction) even for the same foreign particle due to existence of shading as shown in FIG. 29 and it is impossible to detect foreign particles stably by binarization by the threshold value.

In the present invention, as shown in FIGS. 30A–C, shading including the aforementioned (1) and (2) is measured (30A) beforehand using the reference sample 111 shown in FIG. 1, and the corrected data of shading (30B) is obtained by operating the reciprocal of the measured data so as to change the amplifier gain of the detected signal of the detector for each pixel by it, and foreign particles are detected by eliminating the effect of shading (30C). The reference sample 111 is loaded on the inspection stage shown in FIG. 1 or mounted near the inspection stage. However, a structure that the reference sample is loaded on the sample stage in place of the reticle only during shading measurement is possible.

The reference sample 111 is required to have a finely uneven surface and uniform scattering characteristics, and a glass substrate which is polished so as to provide fine defects or a substrate coated with a thin film which can be made finely uneven (for example, an aluminum film deposited on the substrate by the sputtering method) is used. However, it is difficult practically to process fine irregularities on the reference sample 111 uniformly for 1 by 1 μm² pixels. Therefore, the correction data is obtained from the mean value of multi-measurements (for example, 1000 measurements) of shading.

Scattered light from fine irregularities has variations in the intensity. Therefore, a simple mean value (for example, 1000 measured data is divided by 1000) is too small and the operation accuracy may be reduced. Under this condition, it is desirable to set the divisor to each time interval of the measuring count (for example, 200 for a measuring count of 1000). When the shading (30A) before correction is compared with the shading (30B) after correction, as shown in FIGS. 30A–B, the shading before correction which is about 50% is corrected to less than 5%.

When the above corrected data is remeasured and reupdated for each inspection, the optical variable component can be eliminated even if the illumination system and the optical detector system are unstable on a time basis.

FIG. 31 shows a block diagram of a concrete example of a shading correction circuit. The shading correction circuit comprises a subtractor circuit 3209 for subtracting the value of the dark current portion of the one-dimensional imaging device from a value 3212 which is obtained by converting the detected value of the one-dimensional imaging device from analog to digital (256 levels and 8 bits in this case) using data from a memory 3206 controlled by a synchronizing circuit 3205 for each pixel, a multiplier circuit 3210 for multiplying the shading correction magnification by data from a memory 3207 controlled by the synchronizing circuit 3205 for each pixel, and a medium precision bit output circuit 3211 for returning the multiplication result wherein the bits are two times (16 bits in this case) of the bits of the value 3212 which is obtained by converting the detected value of the one dimensional imaging device from analog to digital (256 levels and 8 bits in this case) to the previous bits (8 bits in this case). As shown in the drawing, this example is an example that the shading is corrected by a digital circuit. However, the same result can be obtained by correcting the shading analogically before A-D conversion.

When foreign particles are decided, for example, in units of a 2 by 2 $\mu m^2$ pixel and there are foreign particles more than 2 $\mu m$ in size, the number of pixels wherein foreign particles are detected is different from the actual number of foreign particles. Assuming that a 10-$\mu m$ foreign particle exists, it results in that the foreign particle is detected by about 25 ($(10 \, \mu m/2 \, \mu m)^2$) pixels. Therefore, to observe the detected foreign particle, it is necessary to confirm all the 25 detected results, causing a fault.

This fault is eliminated conventionally by a grouping processing function for checking the link condition of pixels wherein foreign particles are detected and for deciding that one foreign particle is detected when the pixels are neighboring with each other on a software basis. However, this method causes a new fault that since processing by software is necessary, a lot of time is required for the processing when many signals are detected (about 10 minutes for 1000 detected signals).

In the present invention, therefore, the entire detection area is divided into blocks with a field range (for example, 32 by 32 $\mu m^2$) which can be observed at a time and detected signals in one block are all decided as signals from the same foreign particle (block processing). By doing this, even a large foreign particle can be put into the field range at a time regardless of the shape thereof to observe and confirm.

The block processing is simple grouping processing from a view point of function and has a characteristic that it can be easily realized as hardware. According to the present invention, signals are processed in real time using hardware of the block processing and the throughput of the apparatus including the inspection time can be extremely improved (less than ⅔ of the conventional time for 1000 detected signals).

Figure 32:
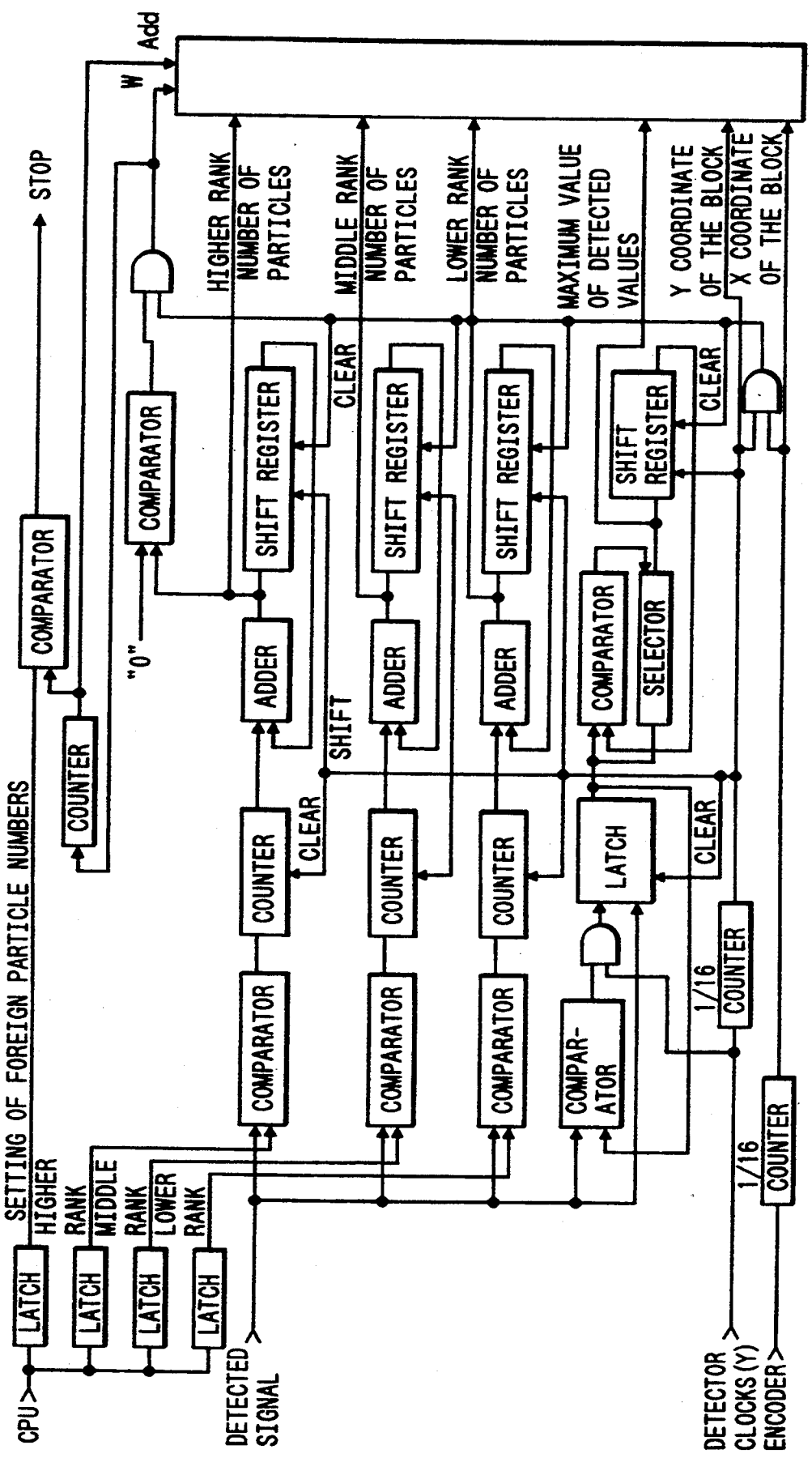
FIG. 32 is a block diagram of an example of a block processing circuit.

FIG. 32 shows a block diagram of an example of a block processing circuit.

In the example shown in FIG. 32, not only decision of the same foreign particle but also the number of detected signals which is a ground for the decision can be classified and counted by large, medium, and small threshold values which are set beforehand and the maximum value of the detected signals in the block can be known. From these data, the rough size of each foreign particle and the status that a plurality of foreign particles are contained in one block can be inferred. Furthermore, a circuit for outputting an inspection stop signal when the number of signals detecting foreign particles reaches the predetermined value is incorporated.

Figure 33:
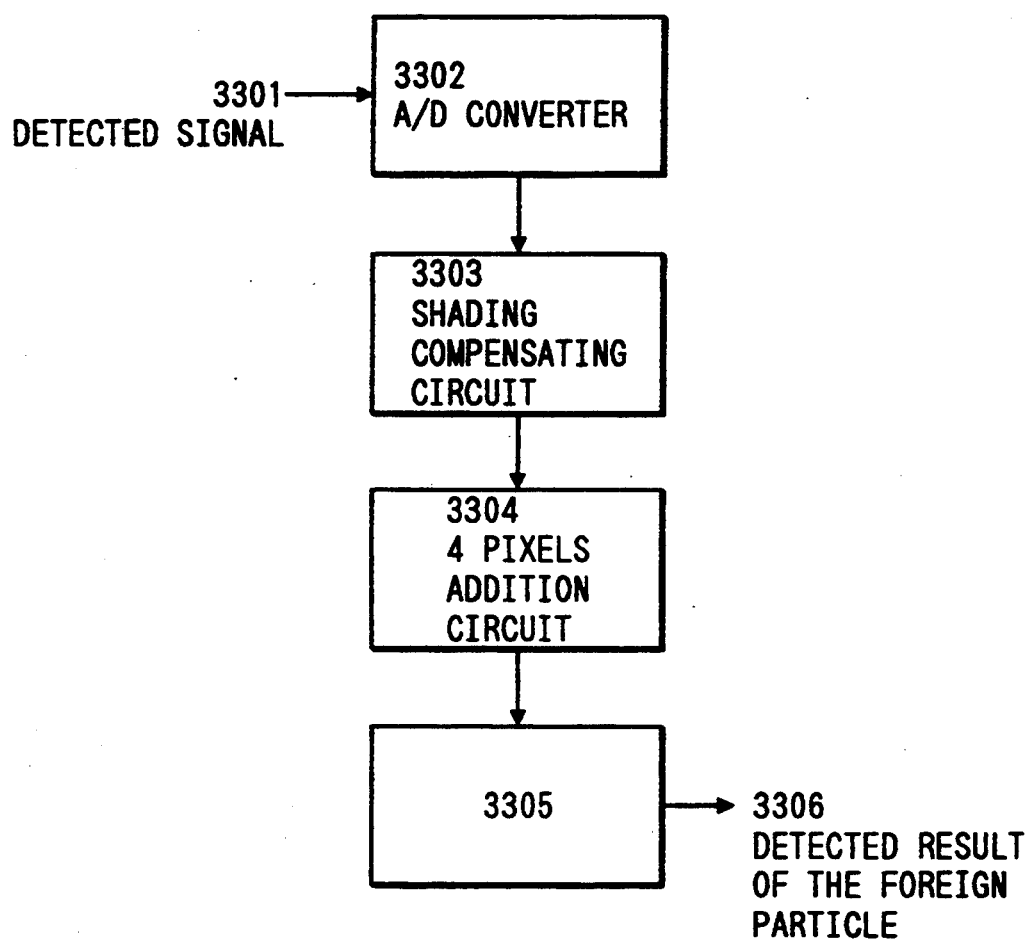
FIG. 33 is a block diagram showing an example of the relation between the shading correction circuit, 4-pixel addition circuit, and block processing circuit.

FIG. 33 is a block diagram showing an example of the relation between a shading correction circuit, 4-pixel addition circuit, and block processing circuit. In the drawing, a detected signal 3301 passes through an A-D converter 3302, and is processed by a shading correction circuit 3303, a 4-pixel addition circuit 3304, and a block processing circuit 3305, and outputs a foreign particle detected result 3306.

As explained above in detail, the present invention provides a foreign particle inspection apparatus which separates and detects small foreign particles of the order of submicrons adhered on a transparent or opaque substrate having a circuit pattern, particularly a circuit pattern such as a reticle, etc. having a phase shift film for improving the patterning resolution easily and stably from the circuit pattern using a simple optical structure principally.

What is claimed is:

1. A foreign particle inspection apparatus for detecting foreign particles adhered on a substrate having a circuit pattern such as a photomask or reticle, comprising:

an inspection stage having a stage for loading and moving said substrate and a drive control system thereof;

an illumination system for illuminating said circuit pattern slantwise;

a means for condensing scattered light and diffracted light generated at the same location of said circuit pattern by illumination of said illumination system by an optical system with a numerical aperture (NA) of more than 0.4;

a spatial filter which is installed on a Fourier transform plane of said optical system and shields diffracted light from a line part of said circuit pattern;

a detection optical system for imaging said circuit pattern on the basis of said condensed and shielded light;

a detector installed on the imaging plane by said detection optical system;

a means for correcting detected values of said detector according to uneven illumination by said illumination system;

a means for obtaining the added value of the detected values of 2 by 2 pixels among said detected values;

a means for obtaining the maximum value of four added values which are shifted pixel by pixel in the four directions around each detector pixel;

a means for binarizing output of said detector; and a signal processing means for digitally processing data from said foreign particles on the basis of said binarized signal.

2. A foreign particle inspection apparatus for detecting foreign particles adhered on a substrate having a circuit pattern such as a photomask or reticle, comprising:

an inspection stage having a stage for loading and moving said substrate and a drive control system thereof;

an illumination system for illuminating said circuit pattern slantwise;

a means for condensing scattered light and diffracted light generated at the same location of said circuit pattern by illumination of said illumination system;

a detection optical system for imaging said circuit pattern on the basis of said condensed light;

a detector installed on the imaging plane by said detection optical system;

a means for correcting detected values of said detector according to uneven illumination by said illumination system;

a means for obtaining the added value of the detected values of 2 by 2 pixels among said detected values;

a means for obtaining the maximum value of four added values which are shifted pixel by pixel in the four directions around each detector pixel; and a signal processing means for processing data from said foreign particles on the basis of said obtained signals.

3. A foreign particle inspection apparatus for detecting foreign particles existing on a mask which has an opaque circuit pattern formed on a front surface of a transparent or semitransparent substrate, the apparatus comprising:
- a moving stage means for moving the mask in X and Y-axis directions;
- a plurality of illumination means for illuminating a plurality of focused laser beams from a direction inclined with relation to a vertical direction of a front surface of the mask formed with the opaque circuit pattern, onto the front surface of the mask;
- a rear detection optical system provided at a rear side of the mask so that an optical axis of the rear detection optical system is substantially vertical to the rear surface of the mask, said rear detection optical system condensing diffracted light generated on the front surface of the mask through the transparent or semitransparent substrate from a portion between the opaque circuit pattern, and for imaging said diffracted light condensed onto an image plane;
- a rear spatial filter means for shielding diffracted light generated by line edges of said opaque circuit pattern through the transparent or semitransparent substrate from the portion between the opaque circuit patterns, the rear spatial filter means being located on a Fourier transform plane of said rear detection optical system;
- a rear detector for detecting the image of the diffracted light obtained through the rear spatial filter means as an image signal, the rear detector being located on the image plane; and
- a rear signal processing means for obtaining information of the foreign particles in accordance with said image signal detected by the rear detector, said rear signal processing means including a circuit for correcting detected values of the rear detector according to uneven illumination, a circuit for obtaining on added value of the detected values of 2 by 2 pixels, and a circuit for obtaining a maximum value of four added values which are shifted pixel by pixel-in four directions around each detector pixel.

4. A foreign particle inspection apparatus according to claim 3, wherein said rear signal processing means further comprises a circuit for storing data in a memory wherein said substrate is divided into blocks every several hundreds of pixels.

5. A foreign particle inspection apparatus according to claim 3, wherein said rear signal processing means further comprises a circuit for storing the detected result in a memory wherein said substrate is divided into blocks every several hundreds of pixels.

6. A foreign particle inspection apparatus according to claim 3, wherein said rear signal processing means further comprises a means for storing the detected result in a memory wherein said substrate is divided into blocks every several hundreds of pixels.

7. A foreign particle inspection apparatus according to claim 3, wherein said rear detection optical system has a numerical aperture (NA) of 0.4 to 0.6.

8. A foreign particle inspection apparatus according to claim 3, wherein the mask has a phase shifter film on a predetermined portion between the opaque circuit pattern, said rear detection optical system having means for shielding a diffracted light generated on the edge of the phase shifter film by the opaque circuit pattern.

9. A foreign particle inspection apparatus according to claim 3, wherein said rear detector has a pixel being less than 4 $\mu m \times 4$ $\mu m$.

10. A foreign particle inspection apparatus according to claim 3 further comprising:
- a front detection optical system provided at a front side of the mask so that an optical axis of the front detection optical system is substantially vertical to the front surface of the mask, said front detection optical system condensing diffracted light generated on the front surface of the mask and for imaging the condensed diffracted light onto an image plane;
- a front spatial filter means for shielding diffracted light generated by the line edges of said opaque circuit pattern, said front spatial filter means being located on a Fourier transform plane of said front detection optical system;
- a front detector for detecting the image of the diffracted light obtained through the front spatial filter means as an image signal, the front detector being located on the image plane; and
- a front signal processing means for obtaining information of the foreign particles, whose size are more than 0.8 $\mu m$ existing on the opaque circuit pattern, in accordance with said image signal detected by the front detector.

11. A foreign particle inspection apparatus according to claim 3;
wherein said plurality of illumination means comprises a laser source for generating said each of focused laser beams having a wavelength less than 660 nm.

* * * * *